United States Patent [19]

Crooks et al.

[11] E Patent Number: Re. 33,259

[45] Reissued Date of Patent: Jul. 10, 1990

[54] METHOD AND APPARATUS FOR RAPID NMR IMAGING OF NUCLEAR PARAMETERS WITH AN OBJECT

[75] Inventors: Lawrence E. Crooks, Richmond; John C. Hoenninger, III, Oakland; Mitsuaki Arakawa, Hillsborough; Jerome R. Singer, Berkeley, all of Calif.

[73] Assignee: The Regents of the University of California, Oakland, Calif.

[21] Appl. No.: 191,025

[22] Filed: May 6, 1988

Related U.S. Patent Documents

Reissue of:

[64] Patent No.: 4,471,305
Issued: Sep. 11, 1984
Appl. No.: 331,008
Filed: Dec. 15, 1981

U.S. Applications:

[63] Continuation-in-part of Ser. No. 926,571, Jul. 20, 1978, Pat. No. 4,297,637, and Ser. No. 120,875, Feb. 12, 1980, Pat. No. 4,318,043.

[51] Int. Cl.[5] ..... G01R 33/20

[52] U.S. Cl. ..... 324/309; 324/307

[58] Field of Search ..... 324/300, 307, 309

[56] References Cited

U.S. PATENT DOCUMENTS

| | | | |
|---|---|---|---|
| 3,651,396 | 3/1972 | Hewitt | 324/314 |
| 4,115,730 | 9/1978 | Mansfield | 324/309 |
| 4,322,684 | 3/1982 | Hounsfield | 324/309 |
| 4,458,203 | 7/1984 | Young | 324/309 |

FOREIGN PATENT DOCUMENTS

| | | |
|---|---|---|
| 1310410A | 3/1973 | United Kingdom . |
| 1496886A | 3/1975 | United Kingdom . |
| 1580787 | 4/1977 | United Kingdom . |
| 2026172A | 7/1978 | United Kingdom . |
| 2052753A | 4/1980 | United Kingdom . |
| 2057142A | 8/1980 | United Kingdom . |
| 1596160A | 8/1981 | United Kingdom . |
| 1601816A | 11/1981 | United Kingdom . |
| 2091884A | 8/1982 | United Kingdom . |
| WO81/027-88A | 3/1981 | World Int. Prop. O. . |
| WO81/027-89A | 3/1981 | World Int. Prop. O. . |

OTHER PUBLICATIONS

*In Vivo Imaging of the Rat Anatomy with Nuclear Magnetic Resonance*, Hansen et al, Radiology 136, Sep. 1980, pp. 695–700.

*Tomography of Hydrogen with Nuclear Magnetic Resonance*, Crooks et al, Radiology 136, Sep. 1980, pp. 701–706.

J. Phys. E.: Sci. Instrum., vol. 13 (1980), pp. 697–707.

"Biological and Medical Imaging by NMR" by Mansfield et al, Journal of Magnetic Resonance 29 (1978), pp. 355–373 (particularly pp. 363–367).

"Effects of Diffusion on Free Precession in Nuclear Magnetic Resonance Experiments" by Carr et al, Physical Review 94, vol. 94, No. 3, May 1, 1954, pp. 630–638 (see FIG. 6).

*Primary Examiner*—Michael J. Tokar

*Attorney, Agent, or Firm*—Nixon & Vanderhye

[57] ABSTRACT

An imaging NMR scanner obtains plural spin echo signals during each of successive measurement cycles permitting determination of the T2 parameter for each display pixel after but a single measurement sequence. The amplitude of the NMR spin echo responses is dependent on an "a" machine parameter (the elapsed time between initiation of a given measurement cycle and the occurrence of the NMR response) and upon a "b" machine parameter (the elapsed time between initiation of successive measurement cycles). These a and b machine time parameters are selectively controlled to enhance resultant image contrast between different types of tissue or other internal structures of an object under examination. Special phase control circuits ensure the repeatability of relative phasing between successive NMR responses from the same measured volume and/or of reference RF signals utilized to frequency translate and synchronously demodulate the NMR responses in the successive measurement cycles of a complete measurement sequence. Special sub-sequences of four measurement cycles are utilized to provide resultant combined spin echo measurements substantially independent of FID signal components.

46 Claims, 11 Drawing Sheets

METHOD AND APPARATUS FOR RAPID NMR IMAGING OF NUCLEAR PARAMETERS WITH AN OBJECT

Matter enclosed in heavy brackets [ ] appears in the original patent but forms no part of this reissue specification; matter printed in italics indicates the additions made by reissue.

This application is a continuation-in-part of our earlier copending, commonly assigned application Ser. No. 926,571, filed July 20, 1978 (now U.S. Pat. No. 4,297,637) and Ser. No. 120,875, filed Feb. 12, 1980 (now U.S. Pat. No. 4,318,043). The entire specification and drawings of each of these earlier related copending applications is hereby expressly incorporated by reference.

This invention relates to apparatus and method for NMR (nuclear magnetic resonance) imaging wherein data representing the internal distribution of selected molecular structures within an object under test is obtained using nuclear magnetic resonance phenomena.

NMR imaging is based on the ability to induce and monitor radio frequency (r.f.) resonance of the magnetic moment of selected nuclei in the presence of magnetic fields. By the use of position-variant magnetic fields, it is possible to measure both the location and concentration in small volumes of resonant nuclei and, thereby, to create a visual display image that reflects this distribution in living tissue (e.g., a human body) or in other internal structures of an object under examination. Hydrogen, because it is in the most sensitive of the stable nuclei to NMR phenomena and because it is also the most abundant nucleus in the human body, is ideally suited for NMR imaging. NMR imaging is a non-invasive diagnostic technique having some general similarity to computed tomography scanning (utilizing X-ray radiation) albeit it is based upon an entirely different physical phenomenon.

A detailed explanation of the particular NMR spin echo phenomena and line volume scanning techniques presently preferred for use with this invention is already set forth in our earlier referenced copending applications. Nevertheless, a brief review of some salient points is included here.

The basic NMR phenomenon is the property of all nuclei having an odd number of protons and/or neutrons to act as small magnets. In the absence of an applied magnetic field, the magnetic axes of these nuclei point in random directions; however, when placed in a strong applied static magnetic field, these axes tend to align with the field. If radio frequency energy of the proper resonant frequency and having its r.f. magnetic field component perpendicular to the static magnetic field is then transmitted throughout the object under test, the resonant nuclei will nutate (e.g. turn) their magnetic axes (e.g., "flip") against the applied static magnetic field. If such radio waves are then terminated (e.g., such as by termination of an appropriate RF pulse), the magnetic axes of the earlier "flipped" nuclei tend to relax back toward their original alignment with the applied static magnetic field. In doing so, radio frequency waves (of the same frequency as that applied in the earlier flipping r.f. pulse if the magnetic field at the nuclei location is unchanged) are emitted and may be detected by an appropriate radio frequency receiver arrangement.

The first and longest NMR r.f. response to appear is the FID (free induction decay). However due to relative dephasing phenomena of the spinning nuclei during the FID it decays and if the dephasing is reversed a so-called spin echo signal can be generated. For example, if a 90° nutation r.f. pulse is first applied, the flipped nuclei will begin to "dephase" in their relative rotational speeds. If after t seconds a 180° nutation r.f. pulse is applied, the dephasing sense of each flipped nuclei is reversed resulting in a "in phase" condition after another t seconds. This "in phase" condition results in a detectable pulse of r.f. energy known as a spin-echo.

Because there are known relationships between the strength of applied magnetic fields and the frequencies of resultant NMR responses, this NMR excitation/detection sequence can be utilized to obtain basic information concerning the location and distribution of specific nuclei within an object under test.

For example, in any given magnetic field, the frequency of transmitted RF energy required to produce NMR is specific (hydrogen in a magnetic field of about 3.5 KG will resonate at about 15 MHz.) For all types of nuclei, the so-called Larmor resonant frequency changes in direct ratio to changes in the strength of the surrounding field at the nucleus site. For instance, hydrogen in a magnetic field of about 7 KG exhibits NMR at about 30 MHz. The constant of proportionality between NMR frequency and the instantaneous magnetic field strength at the location of the nucleus is called the magnetogyric ratio and each specific nucleus having an odd number of protons and/or neutrons has its own respectively corresponding magnetogyric ratio constant.

Actually, it is believed that only a very small fraction (e.g., two or three parts per million) of the relevant nuclei within a given measurement volume actually generate the observed NMR phenomenon at any given instant of time. This is apparently a statistical process and the actual nuclei being observed will change over time but sufficient numbers of nuclei are observed at any given instant of time so as to permit significant NMR measurements.

The elapsed time required to obtain maximum alignment of the nuclei magnetic axes with an imposed static magnetic field is typically on the order of one second for hydrogen in tissue. This exponential NMR alignment time is normally denoted by its exponential time constant "T1" (i.e. the time required to obtain $1-1/e$ of the asymtote or final expected value) and is sometimes known as the longitudinal magnetic relaxation time or as the spin-lattice magnetic relaxation time. It is a function of many local physical and chemical factors including molecular structure, elemental composition, temperature and viscosity. In general, even if only hydrogen nuclei are observed in an NMR imaging scanner, and even if it is assumed that all tissues have equal hydrogen densities, the measured T1 NMR parameter may be expected to differ significantly between different body tissues.

The rate at which NMR signal emission decays is another characteristic exponential time factor and is usually less than the T1 value. This second NMR time factor is commonly referred to by its exponential time constant "T2" and is sometimes known as the transverse magnetic relaxation time or spin-spin magnetic relaxation time. It constitutes another NMR time parameter that is dependent not only upon the identity of the nucleus involved but upon local physical and chemical factors including molecular structure, elemental composition, temperature and viscosity (not necessarily in exactly the same way as is the T1 parameter however). Accordingly, the T2 parameters are in general also different for different body tissues. For example, the nuclei of very pure liquids, in general, align with an applied static magnetic field less quickly and emit NMR signals for a longer time than do nuclei of liquids loaded with proteins.

Since the time constants associated with NMR phenomena are quite long compared to readily achievable response times of electronic circuits (i.e., radio frequency and magnetic gradient coil), it is possible to use a succession of different magnetic gradients and RF pulses to selectively produce NMR signal responses that can be detected and associated with specific elemental internal volumes of an object under test. For example, assume that an object is placed in a strong uniform static magnetic field. After one or two seconds, a significant proportion of the nuclei will have aligned their magnetic axes with the static magnetic field. Further assume that a magnetic gradient along on axis of a three-dimensional system (e.g., the Z axis) is temporarily superimposed on the static magnetic field so as to cause a different magnetic field to exist throughout each successive plane transverse to the Z axis. By choosing a specific frequency, strength and duration for an applied RF pulse, a specific planar volume of these hydrogen nuclei can then be flipped by 90°. At a time t thereafter, further assume that the first magnetic gradient has been switched off and that a second magnetic gradient orthogonal to the first (e.g., along the Y axis) is superimposed upon the static magnetic field. Under these circumstances, the hydrogen nuclei in a planar volume transverse to the Y axis can be addressed by choosing a particular frequency, strength and duration for another RF pulse which may flip the addressed nuclei by 180°. In accordance with the "rule of equal times" (as explained in our earlier-referenced copending applications) an NMR spin echo signal will appear at 2t elapsed time from initiation of this measurement cycle (by application of the first 90° flipping pulse of RF energy).

If, while monitoring this spin echo signal with an RF receiver, the second magnetic gradient field is also switched off and a third magnetic gradient along another mutually orthogonal axis (e.g., the X axis) is switched on, then a different NMR spin echo response frequency will emanate from each elemental volume along the line volume which is caused to emit spin echo signals (due to the intersection of the two earlier selected planar volumes). In this manner, the amplitude of each frequency component of the spin echo signal (as determined by Fourier analysis) represents a nuclear measurement associated with a respective incremental volume of the measured object. This particular measurement cycle can be extended to obtain further spin echo signals by the application of additional RF pulses and magnetic gradients as explained in our earlier copending applications. As also explained in our earlier-referenced copending applications, nuclei dephasing effects caused by the switched magnetic gradient fields may make it desirable to include special phase correcting pulses of magnetic gradients at different times in each measurement cycle. Similar successive measurement cycles are performed to obtain additional spin echo data from the same and from different elemental volumes. The results from the same elemental line volumes are combined (preferably in a special manner to avoid FID signal components) to improve signal-to-noise ratios before being Fourier transformed to provide final data values for each elemental volume along the addressed line volume.

In general, since the frequency of the RF energy required to excite NMR and/or of resultant NMR signals is proportional to the instantaneous magnetic field strength at the measured volume, if the magnetic field strength has a spatial distribution that is known, then the frequency spectrum of NMR excitation/detected signals also encodes the spatial distribution of the NMR nuclei.

Varying the elapsed time interval between successive excitation of a measured volume will produce different amplitudes of NMR response signals in accordance with the T1 parameters associated with the nuclei of the measured volume. That is, if the interval between successive NMR excitations is relatively short, tissues with longer T1 parameter values will yield relatively less NMR response signal than those with shorter T1 parameter values since the former have less chance to become fully re-aligned with the static magnetic field before a new measurement cycle is initiated. In addition, varying the elapsed time interval between the initiation of a measurement cycle (i.e., the first NMR excitation RF pulse required to eventually result in a desired NMR response signal) and the subsequent occurrence of the desired NMR spin echo response signal will produce different corresponding amplitudes of NMR spin echo response in accordance with the T2 parameters of the tissues in the measured volume. That is, tissues in the measured volume having longer T2 parameter values will provide relatively larger NMR response signals than those having shorter T2 parameter values. It has been discovered that these two elapsed time intervals may be selectively chosen so as to enhance the resulting image contrast between predetermined types of tissue.

Motion factors can also change the resultant NMR signal intensity in a live object. For example, if hydrogen nuclei move through the measurement volume during one measurement cycle (e.g., approximately 35 milliseconds), the potential NMR response signal from these nuclei will be completely lost. On the other hand, if only a fraction of such nuclei remain within the measurement volume during the measurement cycle time, the intensity of NMR response signals will be correspondingly reduced. As should be apparent, the actual reduction in intensity of NMR response signals due to motion factors depends upon the fraction of effected nuclei that are in motion and upon their velocity.

Accordingly, images of an object crosssection constructed from measured intensity of NMR responses represent a complex function of physical characteristics of the tissue and of selectable instrument parameters which can be selectively manipulated, in accordance with this invention, to highlight particular types of tissues (e.g., to selectively enhance contrast between selected tissue types).

The instrumentation for NMR imaging systems reflects the sequence by which nuclear magnetic resonance is achieved. A typical system will include a large magnet to create the surrounding magnetic field, magnetic field gradient producing coils to create a position dependent magnetic field, an RF coil to apply and receive the resonant frequency r.f. signals, electronic circuitry to generate, transmit and record the electromagnetic radiations, and a digital data acquisition, processing, and display system.

The various NMR imaging techniques reflect different methods used to stimulate a defined volume and to analyze the resultant signal, or, in other words, to achieve adequate spatial resolution and meaningful contrast in the NMR image. Some of the variations in imaging techniques will cause the NMR image to change accordingly. Not only is the presence of the signal contingent on the system, but the method used to create the signal affects the signal's intensity and behavior in time. This interdependence between system and object has an important effect on contrast resolution in images.

A variety of different NMR methods to define a measured volume have been developed. All techniques, however, are based on the relationship between RF frequency and magnetic field. Because it is impossible to create a magnetic field with a different strength at every point in space at the same time, all techniques use changing magnetic fields to define volume. Magnetic field gradients can be used during transmission or reception or both.

In 1973 Lauterbur first proposed and demonstrated the use of NMR as a method of obtaining images of hydrogen density spanning whole objects. His technique uses the same type of reconstructions as computed tomography and thus is subject to similar artifact problems in image reconstruction. The use of electronic scanning eliminates moving parts and, as with all NMR techniques, there is no exposure to ionizing radiation.

Two generalized types of techniques have been proposed to eliminate the reconstruction necessitated by Lauterbur's method. In one kind, a "sensitive volume" is defined, and the object is moved to produce a two-dimensional tomogram. While there are no reconstruction artifacts, the object must be moved in the magnetic field. These scan techniques are effective in producing images but are wasteful in terms of the data obtained per unit time.

Complex techniques where data is obtained from many points without motion have been proposed and studied. Hinshaw has developed an alternative type of "sensitive point" which can be electronically scanned through an object to produce a two or three-dimensional image. Several other techniques being developed are selective irradiation, and multidimensional Fourier transforms. With these techniques, spatial resolution of the order of 0.5 mm has been demonstrated for rat-sized objects in images obtained in two minutes.

The NMR imager described in our earlier-referenced copending applications uses electronic selection of a single line volume in the object. A slice in the sample can be excited by exposing the sample to a magnetic field variation and a radio wave such that only the desired plane corresponds to the frequencies of the radio wave. Using different directions of the field variation at different times, two intersecting planes can be excited. The intensities of the two radio waves which excite the planes can be chosen so that a signal known as a spin echo will be emitted at a later time by only the nuclei along the intersection of the two excited planes. The spin echo thus contains information about only the nuclei along a line volume. By applying a field variation along the line during read out, a frequency discrimination of the emitted radio waves is produced along that line. The intensity of each frequency of the spin echo will be a function of the hydrogen density, T1, and T2 of a volume element along the selected line. A map of the hydrogen density modified by T1 and T2 will thus be obtained from the frequency spectrum of the spin echo signal. The relaxation times can be measured by observing signal strength when the relevant T1 and T2 instrument parameters are varied.

In NMR as already explained, each tissue is characterized by three parameters: Hydrogen density (H), and the rate at which the polarization of the hydrogen nuclei changes, given by the two times, T1 and T2. The imaging procedures used result in data that is dependent in a complex manner on all three parameters. The contrast between tissues with different relaxation times can be made large, and the influence of the relaxation parameters on the signal intensity can be used to advantage to obtain additional contrast enhancement. However, the image response to tissue differences are also dependent on the details of the sequence used to obtain the image. A change in the relative contribution of these three factors to an image due to the design and operation of different NMR imagers will change the relative tissue signal intensities. Therefore, although the contrast between organs is large, the results between different systems are not easily comparable.

For the technique used in this invention, the relationship of observed NMR intensity (I) to the three physical parameters (H, T1, T2) is approximately given by:

$$I = Hf(v)\exp(-a/T2)[1-\exp(-b/T1)] \qquad \text{Eq. 1}$$

(Note: Actually, Equation 1 includes a denominator of $1+\exp(-b/T2)\exp(-b/T1)$ which can be assumed as substantially equal to unity for b greater than about 3T2) where I is the NMR intensity in a particular region of the image; H is the local hydrogen density; a is the T2 parameter of the instrument, measured in milliseconds and varied within a broad range (typically 20–60 ms) under computer control; b is the T1 parameter of the instrument, measured in seconds and also computer controlled (typically 0.25–1.5 seconds); f(v) is a function of both the speed with which hydrogen nuclei move through the region being imaged and of the fraction of the total number of nuclei that are moving.

It is clear that if I could be measured for b=infinity and a=0, the result would be Hf(v). In fact, neither of these values can be reached directly. The image that is observed is a distribution of I in space. By obtaining three images (two with different values of the T1 instrument parameter and the T2 instrument parameter held constant, and a third one where, for one value of the T1 instrument parameter, the T2 instrument parameter is changed), arithmetic manipulation yields images of Hf(v), T1, and T2. Using the technique of this invention, sufficient data for this determination can be obtained in only two complete measurement sequences.

In NMR, the signal-to-noise ratio (S/N) in the instrument is dependent on a variety of factors including the strength of the magnetic field, the resolution volume, the total volume of the system, the imaging technique being used, and the imaging time. However, it is important to realize that the value of S/N in the instrument is not equivalent to S/N in the final image. This latter parameter depends on a number of factors, for instance, on both the chosen spatial resolution and on imaging time. The spatial resolution is given by the volume from which signals will be received. Since noise is determined mostly by the instrument, larger volumes produce larger signals and improved S/N. On the other hand, as the size of the resolution volume increases with respect to object size, blurring will decrease contrast in the output image in a predictable manner. Thus, when imaging a small object, a relatively large resolution volume (although it would increase the S/N for the instrument) would have an adverse effect on the S/N of the output image.

Longer imaging times result from using a larger number of signal accumulations in the image formation process (e.g. the combination of more spin echos before Fourier transformations in the exemplary embodiment of this invention). The larger number of data sets thus obtained allow for more accurate averaging of the data. Object motion, though, can negate this advantage.

In general, the signal-to-noise, S/N, for the instrument can be written as $$S/N = sVt^{\frac{1}{2}} = sXYZt^{\frac{1}{2}} \qquad \text{Eq. 2}$$

where s is a constant that represents the sensitivity of the system, V is the resolution element volume, equal to the product of its dimensions X, Y, & Z, and t is the imaging time. The volume term arises from the linear relationship between the number of hydrogen nuclei resonating (i.e., providing signal) in the region of a homogeneous object and the volume of that region. The $t^{\frac{1}{2}}$ term arises from the nature of the noise, which is presumed to be pure "white" noise produced by the electronics, and is consequently averaged to zero as more averages are used resulting in longer measuring periods. Coherent noise, for instance, picked up from a computer clock, will affect the image in a manner not susceptible to elimination through averaging. The term s is a function of the value of the polarizing magnetic field.

To summarize, signal-to-noise in the final image is a folding of the S/N of the instrument and of the object contrast realized by the instrument. Comparison with CT will illustrate the significant effect of intrinsic object contrast on contrast resolution in the final image. Intrinsic tissue contrasts in NMR is considerably higher than that derived from differences in electron density, and, consequently, even though the noise in the NMR system may be greater than in CT, the contrast resolution in the final image will be significantly better than in a comparable CT picture. For example, in CT noise per pixel may be only 0.5%, and the difference between fat and muscle 3.5%, resulting in a S/N of 7 in the final image. In NMR, on the other hand, noise may be as high as 5% per pixel, ten times worse than in CT; however, object contrast between fat and muscle can be as high as 300%, giving an S/N of 70 in the final image—or a contrast resolution ten times better than that found in CT.

Keeping the four parameters of the tissue in mind (H, T1, T2 and movement), resulting NMR intensities from different tissues can be understood. Hydrogen density and movement strongly affect the intensity of signal emitted from:

(a) air, because it has essentially no hydrogen and bone because what hydrogen it has is in a solid matrix, will show no signal at all (except where partial volume effects come into play;

(b) vessels through which blood flows will yield a low density signal, and organs with high blood flow will show a lower and "blotchier" NMR intensity in a live animal when compared to signals that would contain in the dead animal (c) the lung, because of its air content of approximately 70% and high blood flow, will also be of lower intensity than other soft tissues.

T1 and T2 NMR parameters play an important role in distinguishing between soft tissues. The hydrogen content of most soft tissues varies over a range of approximately 20%. Contrasting with this, T1 and T2 vary by factors of up to 500%. Tissues with short T1 and T2 values will tend to yield the largest NMR intensities and because of the exponential nature of the modulation of H, the relatively smaller variations of this latter parameter may be overshadowed by T1 and T2 variations.

Although the NMR intensity image can be considered and "arbitrary" representation of the object (since a different image can be obtained by changing the T1-related and T2-related parameters of the instrument), the image nicely delineates normal anatomy. In addition, pathology is evident and, by manipulating the instrument's parameters, we have discovered that selective enhancement of pathology can be obtained. Finally, T1, T2 and Hf(v) images can be formed from a set of NMR measurements. Although these three images are the most direct representations of the tissue's physical parameters, whether these or I images (with instrument a and b parameters selected for particular diseases) will be diagnostically more useful will be determined through careful studies and experience.

In addition to the NMR spin echo imaging technique described and claimed by us in our earlier referenced copending applications, several other types of NMR imaging apparatuses and methods have been described in the literature as earlier mentioned. Many of those skilled in the art have recognized that the measured T1 and/or T2 NMR parameters (regardless of the particular measurement technique) represent a complex function of local physical and chemical factors which cause them to have different values for different body tissues in spite of the fact that only hydrogen nuclei are being measured in all of the tissues. Thus, it has been recognized that resultant NMR images can be expected to show more than the mere relative numerical distribution of hydrogen nuclei throughout a measured cross-sectional volume and that, in some instances, and image of the T1 parameter values might provide better contrast between different tissues than an image of the T2 values and vice versa. There may also be some general recognition in the art that because the resultant NMR signals are such a complex function of many different parameters, it is conceivable that some of these parameters might be successfully utilized to provide enhanced image contrast. However, none of the prior art is believed to teach the image enhancement apparatus and method based on our NMR spin echo imaging technique as now discovered and as described and claimed herein.

In "Medical Imaging By NMR" by P. Mansfield et al, British Journal of Radiology, Volume 50, pages 188–194, 1977, some of the variations possible with the FID measurement of the T1 NMR parameter are discussed. In particular, at page 190 thereof, it was particularly recognized that the effective measured spin density at a given location depends upon the time delay between successive excitation pulses in accordance with the exponential relationship $[1-\exp(-\tau/T1)]$ where $\tau$ equals the elapsed time delay. Making this observation, Mansfield et al noted that it would be possible for localized regions of the specimen to give an apparent picture brightness less than the actual localized spin density would suggest. They referred to this effect as spin-lattice relaxation time discrimination and alleged that most of the observed intensity variations between tissue types seemed to be attributable to this effect rather than to any real density variations, though if present, these two were said to "aid picture contrast". Continuing, Mansfield et al noted that measured variations in T1 within a given specimen are a reflection of variations in both the mobility of the free water, fat or oil and the concentration of dissolved minerals, nutrients, etc., etc., characteristic of the various tissues. Later on in the same publication, Mansfield et al noted that although no noticeable image discrimination was available between some specimens (e.g., normal and malignant tissues) at certain elapsed time delays between measurement cycles, clear differentiation between those same tissues could be obtained by changing the delay times. However, it should be noted that in this particular article, Mansfield et al are discussing an NMR measurement technique wherein each measurement cycle produces but a single FID (free induction decay) NMR response. There is no discussion of any imaging technique which relies upon spin echo NMR response which provide two simultaneously controllable machine timing parameters as in our presently described technique.

Hinshaw et al in "An In Vivo Study of the Forearm and Hand by Thin Section NMR Imaging", British Journal of Radiology, Volume 52, pages 46–43 (1979), describe a technique where the ratio of T1/T2 parameters is measured. They also note that this ratio can act as a tissue contrast parameter between adjacent tissues having the same proton density but differing T1/T2 ratios. They also suggest varying the nutation angle of the RF excitation pulses to obtain detailed information on the relaxation properties of components in the measured volume and/or to study the dynamic response of the NMR signal.

Tanaka et al in "Non-Invasive Measurement of Biological Information by Nuclear Magnetic Resonance: Measurement of Relaxation Time of a Particular Target by Magnetic Focusing Method", Proceedings of the IEEE, Volume 66, No. 11, Nov. 1978, pages 1582–1583, also recognize that in measuring the T1 parameter, the resulting measured value is a function of the elapsed time between excitation pulses.

With respect to observed differences in image contrast between tissues having differing T1/T2 ratios even though having equal proton densities, reference is also made to Hawkes et al, "Nuclear Magnetic Resonance (NMR) Tomography of the Brain: A Preliminary Clinical Assessment With Demonstration of Pathology", Journal of Computer Assisted Tomography, Volume 4, No. 5, Oct. 1980, pages 577–586. Here again, Hawkes suggests that the dependence of the NMR response to the T1/T2 ratio in individual scans can be varied by varying the degree of nutation (e.g., the transmitted RF pulse length and/or power). Hawkes also indicates that while there is great latitude to alter the contrast parameters in NMR imaging, these are at present chosen empirically, and the ideal setting for different pathological tissues will be determined with the feedback obtained during clinical use of the machine. Without specifically identifying them, Hawkes et al note that "at least four separate variables contribute to the NMR signal" and that "it is likely that future machines will allow the operator several choices of imaging parameters to alter tissue contrast and also include some method of abstracting numerical information from the raw scan data", Ling et al in a May 12, 1980 letter to the Editor ("Comparison of NMR Water Proton's T1 Relaxation Times of Rabbit Tissues at 24 MHz and 2.5 MHz", pages 748–756 of Physics in Medicine and Biology), note that the measured T1 NMR value can change as a function of NMR frequency and that T1 images may display more interesting detail than an actual image of measured proton density.

Using a line volume, spin echo NMR measurement cycle as described in out earlier referenced copending applications, we have now discovered that the measured NMR intensity (assuming no substantial physical motion through the measurement volume of the nuclei under test) is approximately given by the earlier stated Equation 1. It has further been discovered that the a and b machine parameters of this invention can be selectively controlled so as to enhance the resulting available image contrast between selected tissues. For example, if the a and b parameters are chosen correctly, it is conceivable that an optimum contrast image could be obtained in a single complete sequence of measurement cycles obtaining only a single I value for each measured volume. In general, if enhanced image contrast is desired between two tissues having T1′, T2′ and T1″, T2″ NMR parameters, respectively, then the a machine parameter is chosen to be between the T2′ and T2″ values while the b machine parameter is chosen to lie between the T1′ and T1″ values. The optimum a parameter value would be chosen as approximately equal to the quantity $[T2'T2''\ln(T2'/T2'')]/(T2'-T2'')$.

The preferred measurement cycle for use with this invention is presently one which provides two NMR spin echo responses and special sequences of such measurement cycles (e.g., sub-groups of four) are preferably utilized to provide respective spin echo signals that are combined in a manner so as to cancel background FID signal components therefrom when the spin echo signals are averaged prior to being Fourier transformed so as to provide intensity measurements at each elemental measured volume site.

Synchronous frequency translation and demodulation techniques are preferably utilized in the r.f. receiver utilized in the practice of this invention as described in our earlier referenced copending applications. It has also been discovered that relative phase differences in the transmitted RF pulses from one measurement cycle to the next and/or relative phase differences between the reference RF signals supplied to the frequency translation/synchronous demodulation receiver circuitry from one measurement cycle to the next can result in significant errors. Accordingly, the preferred embodiment of this invention includes phase control (e.g., resetting) techniques for accurately controlling the relative phase of transmitted RF fields at the initiation of each transmitted RF excitation pulse. The same or similar phase control techniques are also preferably employed for accurately periodically resetting the relative phase of reference RF signals supplied to the r.f. receiver circuitry.

These and other objects and advantages of this invention will be more completely understood and appreciated by reading the following detailed description of the presently preferred exemplary embodiment of this invention taken in conjunction with the accompanying drawings, of which:

Figure 2:
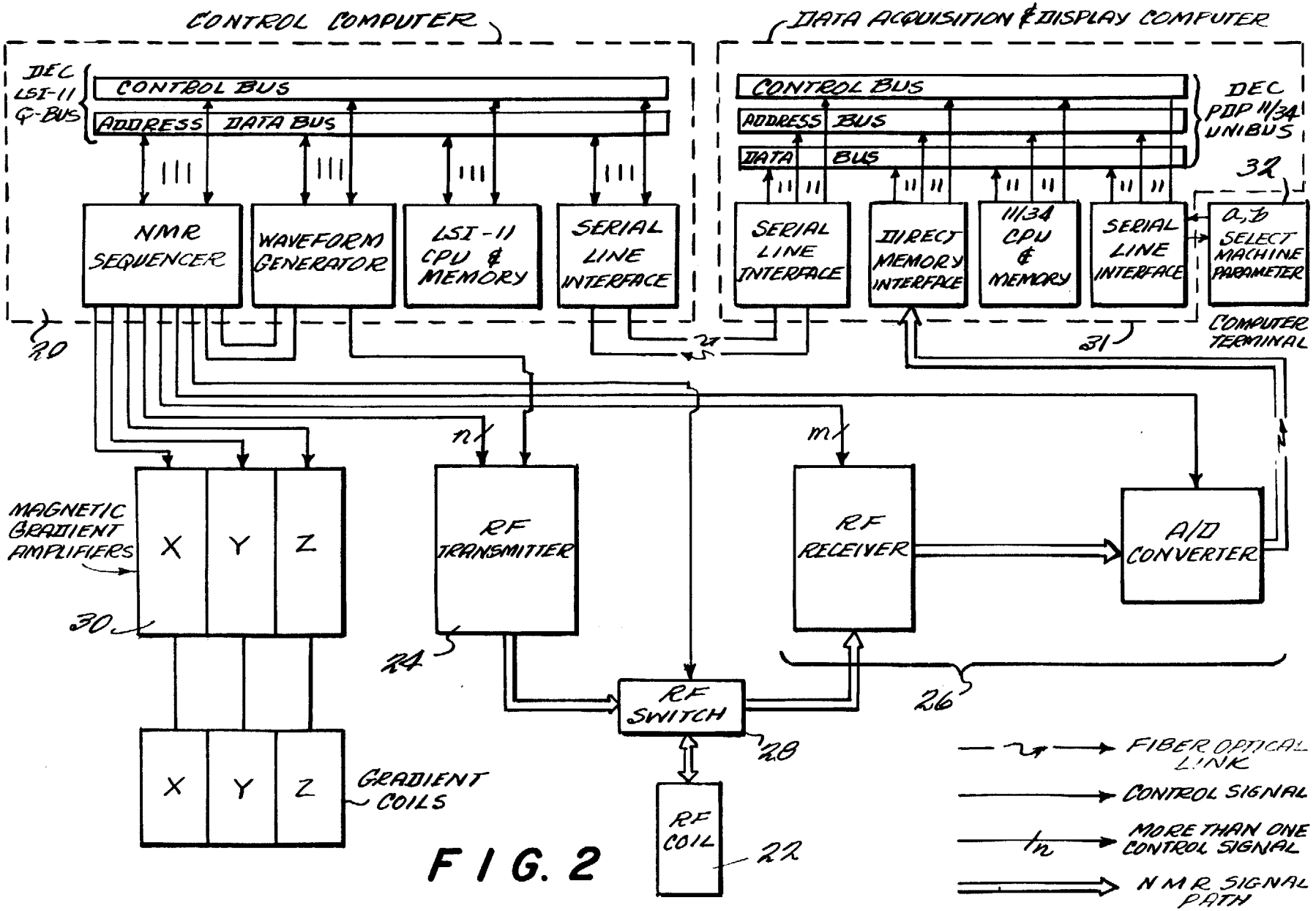
FIG. 2 is a block diagram of the computerized electronic apparatus utilized for driving the magnetic gradient coils and the RF circuits including a transmitting-/receiving RF coil for an exemplary embodiment of this invention.
Figure 4:
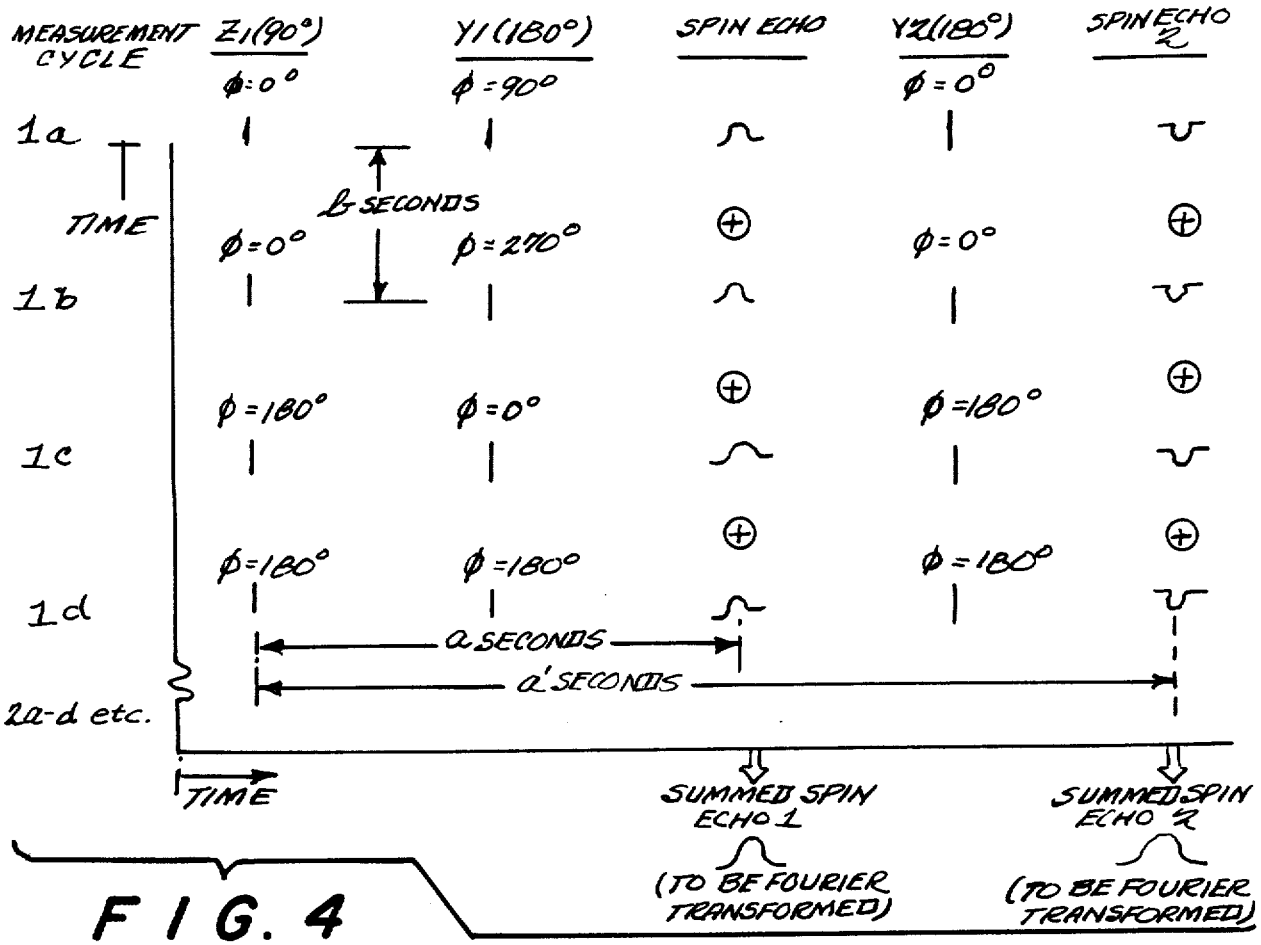
FIG. 4 is a diagrammatic depiction of a complete measurement sequence comprising plural successive measurement cycles, each of which cycles provides plural spin echo NMR response signals in accordance with an exemplary embodiment of this invention.

FIGS. 6A–6E comprise a flow chart description of a suitable program for the computerized control apparatus of FIG. 2 which implements the exemplary sequence of measurement cycles shown in FIG. 4 for selectively varying T1-related and T2-related scanner parameters.

Figure 7:
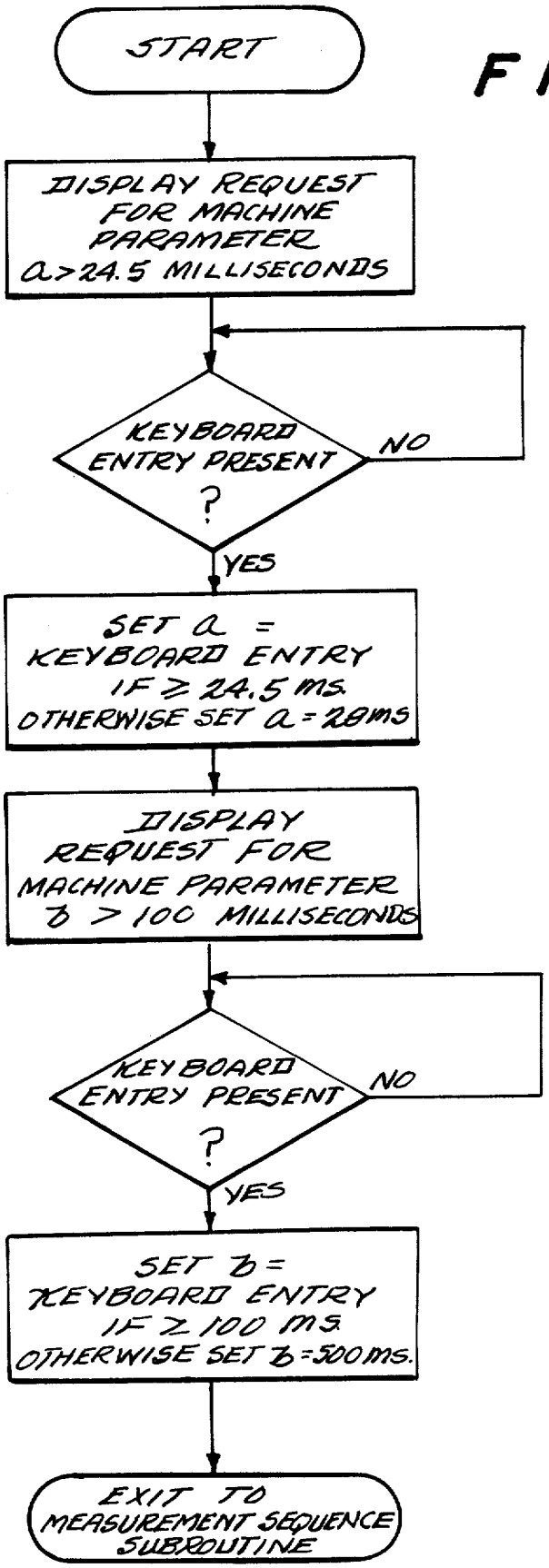
Figure 8:
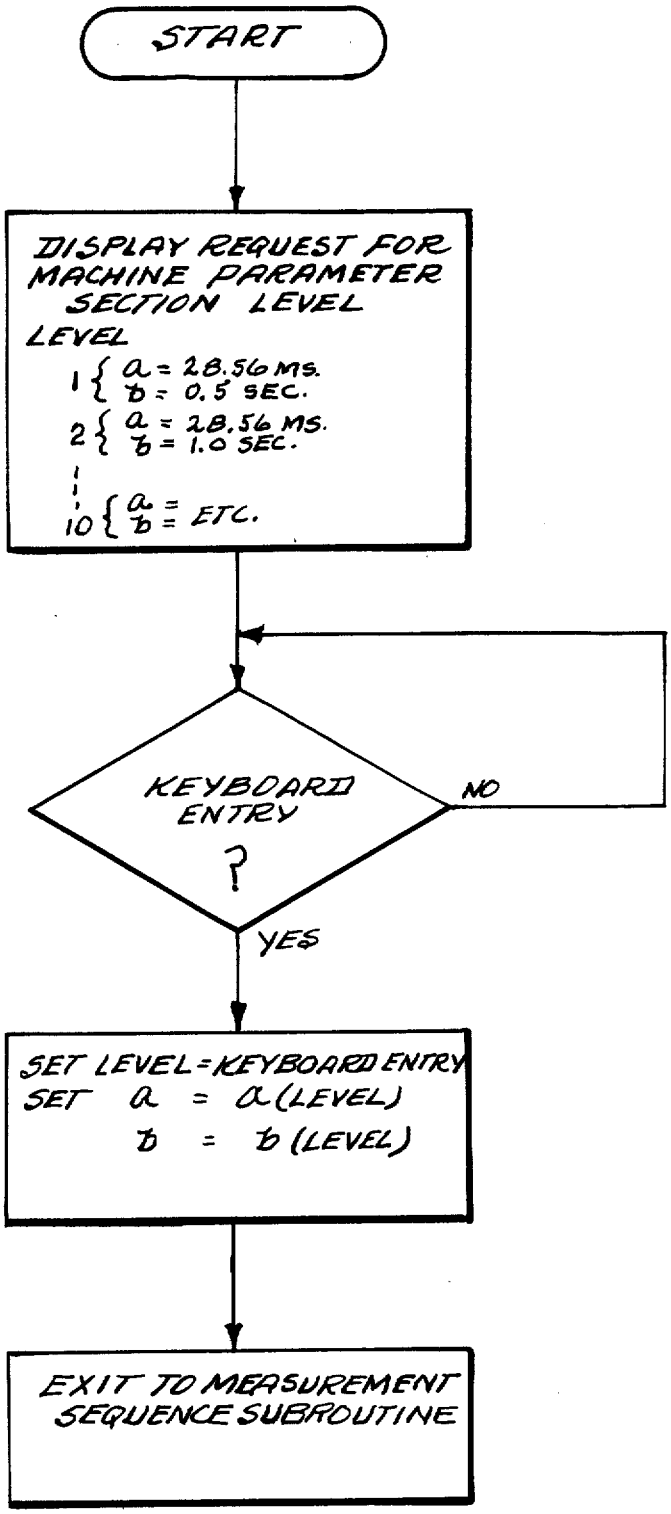

FIG. 7 is a typical executive program permitting selective alteration of the program shown in FIGS. 6A–6E; and FIG. 8 is a typical executive program permitting selective choice of several pre-defined programs of the type shown in FIGS. 6A–6E.

Figure 1:
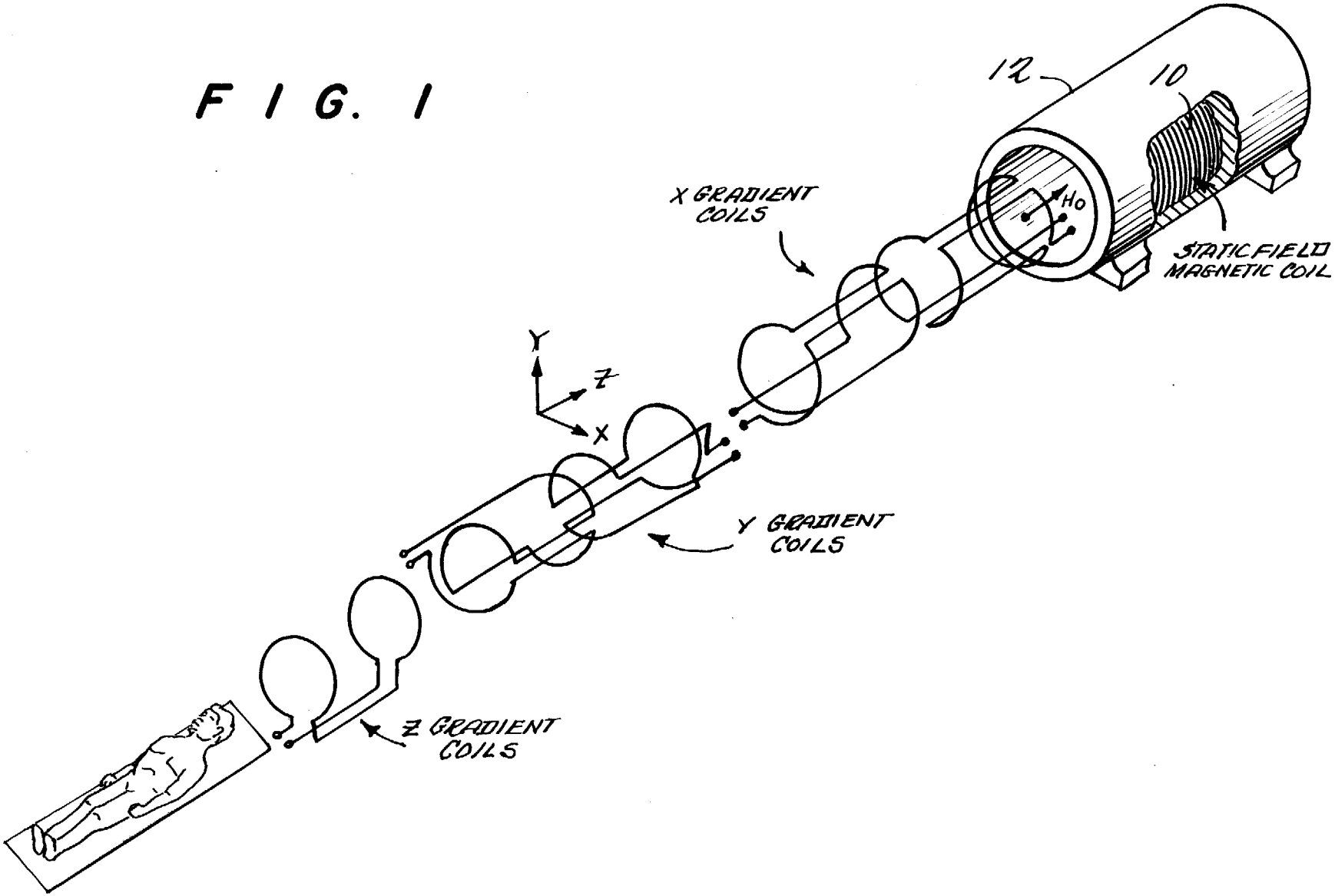
FIG. 1 is an exploded perspective view of a suitable static magnet coil and gradient coils for use with an exemplary embodiment of this invention.

Referring to FIG. 1, the present exemplary embodiment of this invention includes a static field magnetic coil 10 for generating a uniform static magnetic field $H_0$ directed along its axis. The coil 10 is, in the exemplary embodiment, preferably large enough to receive a human body and is preferably surrounded by a cryogenic housing 12 filled with liquid helium or the like so as to permit the coil 10 to be superconducting. In the exemplary embodiment, the static field is of approximately 3.5 KG thus making hydrogen nuclei exhibit NMR at approximately 15 MHz frequency. The X gradient coils, Y gradient coils and Z gradient coils shown in exploded perspective at FIG. 1 are actually concentrically superimposed within the static field magnetic coil 10 and are preferably constructed so as to receive at least a portion of the human body therein. The RF transmit/receive coil (not shown in FIG. 1) is also of conventional design (as are the other coils shown in FIG. 1) and is designed so as to cause the RF magnetic field to be perpendicular to the static magnetic field $H_0$ as will be appreciated by those in the art.

Exemplary electronic apparatus for sequentially driving the various magnetic and RF coils is shown in detail at FIGS. 11A and 11B of our earlier referenced copending applications. For clarity, that apparatus has been shown in simplified form at FIG. 2 of this application and an improved phase-controlling portion of the RF transmitter circuitry is shown in more detail at FIG. 3.

Referring to FIG. 2, a computerized control system 20 is in communication with the data acquisition and display computer 31 via a serial line link. This control system constitutes the NMR system control which controls the amplitude, timing and/or phasing of the necessary transmitted RF pulses, current drives to the magnetic gradient coils and RF detection processes required for NMR. It includes conventional data storage, data output/input and data entry components as appropriate to the requirements of a particular installation. The computer control system 20 typically also comprises plural data processors operating in parallel under control of a host data acquisition and display processor 31 as will be understood from our earlier referenced copending applications. Except for the particular novel time parameter control functions to be performed (e.g. as set forth in the flow diagram of FIGS. 6A–6E), the NMR system control 20 is of conventional design or as described in our earlier referenced copending applications.

Figure 3:
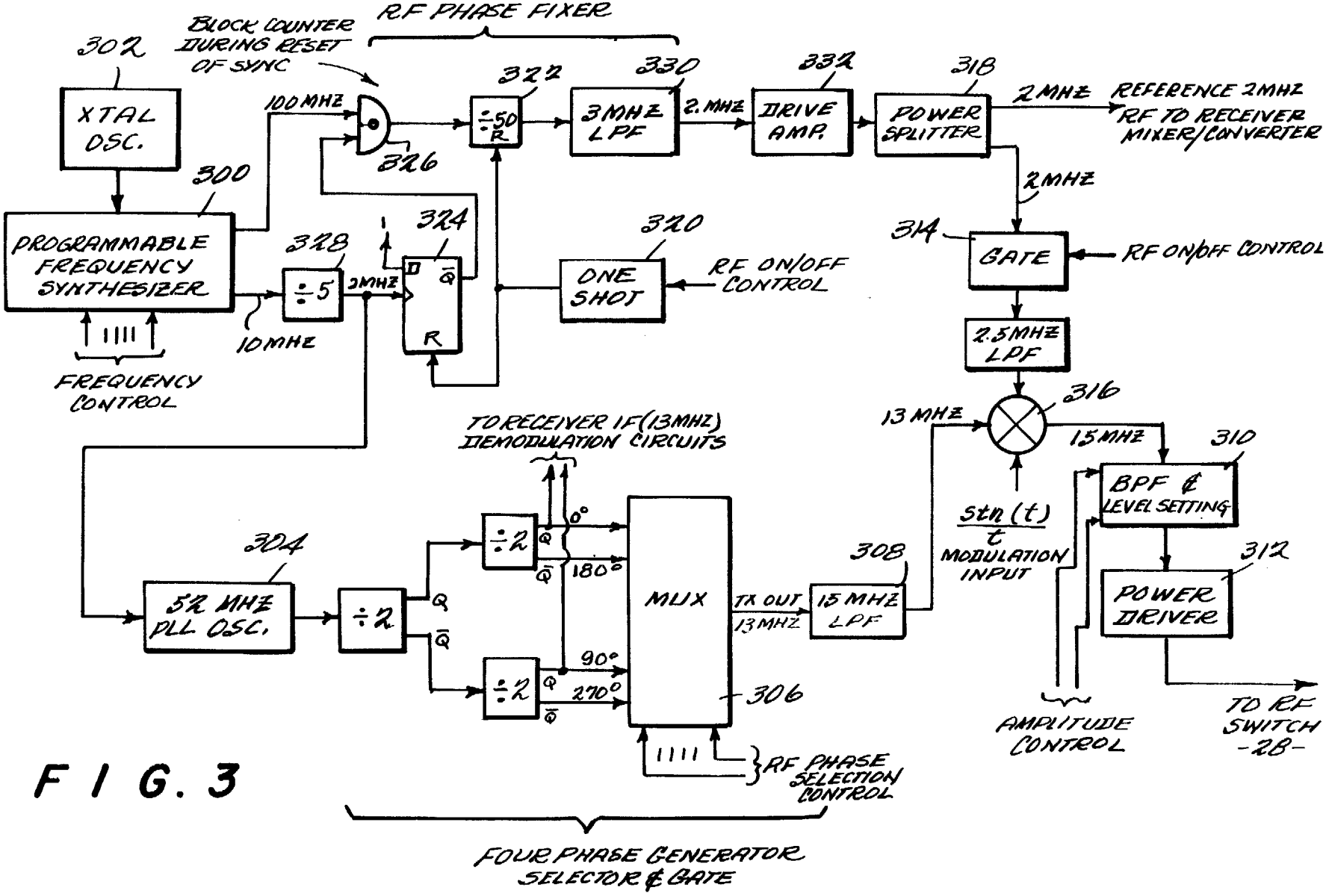
FIG. 3 is a more detailed diagram of relevant phase control portions of the RF transmitter shown in FIG. 2.

The RF coil 22 is of conventional design and is used for both transmitting and receiving RF energy to/from the object under test. It is selectively communicated with by either the RF transmitter 24 or the RF receiver and A/D converter 26 via an RF switch 28 which is, in turn, controlled via a control line by the NMR system control 20. This portion of the apparatus is used for selectively transmitting nutation pulses of RF energy into the object under test (said pulses having programmable amplitude, frequency and duration so as to effect a desired nuclei nutation) and for selectively detecting NMR r.f. spin echo responses from the object under test during programmable listening periods. Except for the improved phase control of the RF signal generator (as depicted in FIG. 3), the RF transmitter 24, RF receiver and A/D converter 26 and RF switch 28 may be of the type described in greater detail in out earlier referenced copending applications.

The magnetic gradient coil drivers 30 are controlled by the NMR system control 20 to selectively drive the X gradient coil, Y gradient coil and Z gradient coil with currents of programmable magnitude, duration, polarity, etcetera all as described in more detail by our earlier referenced copending applications.

Before describing the improved phase control for the RF signal exemplary measurement sequence of FIG. 4 will be explained. In FIG. 4, a complete measurement cycle is shown on one horizontal line with the time scale increasing from left to right. Subsequent measurement cycles are shown on subsequent horizontal lines with the time scale increasing as one proceeds from top to bottom vertically in FIG. 4. Each measurement cycle includes: (1) a 90° nutation pulse Z1 (of programmable relative phase); (2) a 180° nutation RF pulse Y1 (of programmable relative phase); (3) a first NMR spin echo response; (4) yet another 180° nutation RF pulse Y2 (of programmable phase); and (5) a second NMR spin echo signal. The X, Y and Z magnetic gradient pulses necessarily utilized during each of these events are not shown. Nor are the desirable phase correcting magnetic gradient pulses employed in conjunction therewith. It is assumed that the reader will be familiar with the required accompanying encoding magnetic gradient and phase correcting magnetic gradient pulses from our earlier-referenced copending applications.

In the exemplary embodiment, one complete measurement cycle typically comprises approximately 60 milliseconds and produces two NMR spin echo signals having two respectively corresponding different T2-related machine parameters. That is, the first spin echo has a T2-related parameter of "a" milliseconds as measured from the initiation of the measurement cycle (at the midpoint of the first RF nutation pulse) until the midpoint of the first spin echo occurence. The second spin echo has a T2-related parameter of a' milliseconds as measured from the same initiation of the measurement cycle until the midpoint of the second spin echo occurrence.

After a desired delay defining the T1-related machine parameter between initiation of successive measurement cycles (an elapsed time of b seconds), a second measurement cycle is initiated as shown in FIG. 4. As should be appreciated by those in the art, spin echo signals can be expected at predefinable time windows due to the well known "rule of equal times" and the RF receiver is enabled during these windows to sample the received spin echo signals (e.g. typically every 72 microseconds), digitize and store the detected sample amplitude thus effectively digitizing and storing a replica of the detected spin echo signal. To enhance signal to noise ratios and to also cancel residual FID signal components, multiple measurement cycles are performed with the corresponding spin echo signals from several measurement cycles being combined before the resultant spin echo measurements is Fourier transformed in accordance with our earlier referenced copending applications to provide measured NMR response intensities for elemental measured volumes along the selected line volume giving rise to each spin echo signal. For example, to achieve acceptable signal to noise ratios, it is often necessary to combine approximately 12–24 individual NMR responses. Furthermore, as explained in more detail in our earlier copending above-referenced applications, the measurement cycles are preferably combined in groups of four so as to cancel unwanted FID signal components that are inherently measured together with the desired spin echo NMR response.

In particular, by selecting appropriate relative phases of RF excitation pulses, the relative polarity of spin echo and FID signals can be controlled so that when groups of four spin echo signals are combined (by addition and/or subtraction), the unwanted accompanying FID signal components are automatically cancelled. The following Table 1 explains these possibilities for the presently preferred exemplary embodiment. Note that the relative phase of the second 180° nutation RF pulse Y2 is equal to the relative phase of the 90° nutation pulse Z1 in that same measurement cycle and thus need not be included in this table. Also note that this causes the sign of the second spin echo to be opposite that of the first spin echo:

TABLE 1

| | Phase of 90° RF Pulse | Phase of 1st 180° RF Pulse | Sign of spin echo | Sign of x plane FID | Sign of y plane FID |
|---|---|---|---|---|---|
| 1. | 0° | 0° | − | + | − |
| 2. | 0° | 90° | + | + | + Quad |
| 3. | 0° | 180° | − | + | − |
| 4. | 0° | 270° | + | + | − Quad |
| 5. | 180° | 0° | + | − | + |
| 6. | 180° | 90° | − | − | + Quad |
| 7. | 180° | 180° | + | − | − |
| 8. | 180° | 270° | − | − | − Quad |

By inspection of this table and FIG. 4, it will be observed that the first four measurement cycles 1a–1d shown in FIG. 4 correspond to lines 2, 4, 5 and 7 of Table 1. It will also be observed from Table 1 that if the measured spin echo signals are algebraically summed in this example, the unwanted FID components (both x plane and y plane) will automatically be cancelled thus leaving only the desired spin echo signal summed components for later Fourier transformation. Actually, it is preferred that the entries be chosen from Table 1 so as to result in alternating polarity of the spin echo signal (e.g. by choosing lines 1, 2, 5 and 6 which are then combined by selective addition and subtraction to provide a non-zero spin echo measurement). If this is done, then DC errors in the audio frequency portions of the RF (i.e., following demodulation) receiver will automatically cancel thus eliminating the possible necessity of providing DC compensation to such circuits.

The complete measurement sequence of measurement cycles as shown in FIG. 4 preferably include one or more dummy measurement cycles at the very beginning (not shown) so as to ensure that the volume under test has reached its T1 parameter equilibrium for the given choice of the machine b parameter before actual measurement data is taken. For example, if the volume under test has not been excited to NMR in the recent past, and if the b parameter of the machine is not several times larger than the T1 NMR parameter of the object under test (an unlikely condition), then the NMR responses obtained during the first one or so measurement cycles will be relatively greater than those obtained later on in the entire measurement sequence as should be appreciated by those skilled in this art.

For the presently preferred exemplary embodiment, the b parameter of the scanner may be selected as 0.25; 0.5; 1.0 or 1.5 seconds. As should be apparent, the b parameter of the machine is controlled by controlling the delay between initiation of successive measurement cycles while the a parameter is controlled (typically 28 or 56 milliseconds) by controlling the delay between the application of successive RF nutation pulses with due regard for the well known "rule of equal times". One present technique is to produce four images in which a=28 ms and 56 ms and b=0.5 and 1.0 sec. As will be better understood from the following, these four images can be obtained using only two complete measurement sequences in accordance with this invention. These four images of NMR intensity I can be used to calculate images of Hf(v), T1 and T2 using the relationship described in Equation 1. An asympototic I image can also be calculated by setting b=infinity (i.e., no T1-dependence) and using the calculated values of Hf(v), T2 for any desired value of a. Actually, once the two complete measurement sequences have been performed so as to permit calculation of Hf(v), T1 and T2, any desired I image can be calculated using Equation 1 so as to optimize image contrast between selected tissues having differing Hf(v), T1 and T2 NMR parameters.

While the b parameter of the machine can never be less than the length of one complete measurement cycle, it is relatively easy to control so as to have any greater desired value. On the other hand, the a parameter of the machine is somewhat more difficult to vary because of the required pulse rise times associated with the current driving of the gradient magnetic coils. To minimize the a parameter of the machine, it may be necessary to optimize the gradient coil driving circuits so as to minimize the rise and fall times associated with the driving current pulses supplied to these coils. However, such optimization is in accordance with well known standard electrical engineering practices.

It should be noted that because each measurement cycle in the preferred embodiment of FIG. 4 includes two NMR responses, each having different T2-related machine parameters a and a' respectively, it is possible to calculate the T2 NMR parameter of the object volume under test from a single measurement sequence (e.g., by test fit to an exponential curve). To obtain the T1 NMR parameter value for the object under test (e.g., by best fit to an exponential curve), it is necessary to perform one additional complete measurement sequence using a different T1-related machine parameter b. Nevertheless, in contrast to many other measurement techniques, it is a decided improvement to achieve a measurement of both the T1 and T2 NMR parameters of an object under test with only two complete measurement sequences. With other techniques, it is usually necessary to perform three or four complete measurement sequences to obtain enough information to determine the T1 and T2 NMR parameters of an object under test.

Because spin echo signals from different measurement cycles are combined in the exemplary embodiment before Fourier transformation, it has been discovered that improved system performance can be obtained if the relative phase of the RF excitation signals (and of reference RF signals used for frequency translation and synchronous demodulation in the receiver circuitry) are accurately controlled and phased relative to the initiation of each RF pulse and/or RF detection window. To achieve this precise phase control with respect to the on/off control of RF pulses, the RF transmitter 24 has been modified as shown in FIG. 3.

A programmable frequency synthesizer 300 is conventionally driven by crystal oscillator 302 and by digital frequency control signals from the NMR system control 20 to provide output signals of different frequency as required to address the Larmor frequencies of selected line volumes of nuclei as should be apparent. Since the approximate center Larmor frequency involved in the scanning of the exemplary embodiment is 15 MHz, the explanation of the RF signal generating circuitry shown in FIG. 3 will be made at this center frequency. However, it should be understood that the actual frequency of operation will be shifted from this center frequency (both up and down) as necessary to address selected line volumes of nuclei in accordance with the teaching of our earlier referenced copending applications. For example, the frequencies may be shifted at 1 kilohertz steps on either side of the 15 MHz center frequency.

At the center frequency operating point, the programmable frequency synthesizer 300 produces synchronous 100 MHz and 10 MHz output signals. The 10 MHz output is divided by 5 to provide a 2 MHz reference signal used to control a 52 MHz phase locked loop oscillator 304. The 52 MHz output is then divided by 4 to provide a 13 MHz IF signal. As shown in FIG. 3, three flip-flops or divide by two circuits are utilized to provide 13 MHz IF signals at 0°, 90°, 180° and 270° relative phase. One of these four available 13 MHz IF signals is then selected by the multiplexer 306 under control of the NMR control computer 20. The 0° and 90° phase 13 MHz IF outputs are provided to the synchronous demodulator circuits of the receiver. The multiplexer selected 13 MHz IF output is then passed through a low pass filter 308 and mixed with a 2 MHz signal to provide a 15 MHz NMR excitation signal. As explained in our earlier referenced copending applications, this excitation RF signal is preferably modulated by a sinc(t) function before passage through a band pass filter and level setting circuitry 310 and on to power drivers 312 and, through the RF switch 28, to drive the RF coil 22.

An RF excitation pulse of the proper width is produced by an RF on/off control signal in conjunction with the gate 314 which only passes the 2 MHz conversion signal to mixer 316 for the desired pulse duration. In addition, suitable amplitude control can be provided to the level setting portion of circuits 310 if desired under control of the computer control system 20.

As shown in FIG. 3, a 2 MHz reference signal is generated and, after splitting at 318, is provided both to the receiver IF mixer/converter and to the transmitter mixer/converter 316. By carefully controlling (e.g. resetting) the phase of this 2 MHz reference signal, the relative phase of both the transmitted RF signals and of the reference RF signal provided to the receiver mixer/converter can be carefully controlled so as to provide more precisely repeatable NMR pulse echo measurements during successive measurement cycles.

In the exemplary embodiment of FIG. 3, this precise phase control is obtained by an "RF phase fixer" which utilizes a relatively high frequency output from the frequency synthesizer (e.g. 100 MHz) and a resettable frequency divider. In particular, the RF on/off control signals from the NMR system control 20 are presented to a one-shot 320 which preferably triggers on both positive going and negative going transitions. When triggered, on-shot 320 resets counter or frequency divider 322 and flip-flop 324. The Q output of flip-flop 324 also blocks gate 326 so as to hold the counter 322 in a fixed state until the next 2 MHz signal transition coming from divider 328. At that precise instant (always in phase synchronism with the 0°, 90° 13 MHz IF reference signals provided to the receiver), gate 326 is permitted to pass the 100 MHz output of the frequency synthesizer 300 which, after division by 50 and passage through a low pass filter 330, provides a 2 MHz output. The 2 MHz output from the low pass filter 330 is then amplified at 322 and passed on to the power splitter 318 to provide the 2 MHz frequency conversion signals previously described.

Accordingly, at the initiation time of each RF excitation pulse, the RF reference and transmitted signals are mutually reset and synchronized with one another. Additionally, since one-shot 320 also triggers at the termination of each RF on/off excitation control pulse, these same RF signals are similarly reset in phase at the termination of each transmitted RF pulse thus ensuring proper frequency conversion and synchronous demodulation in the receiver circuitry in a manner that is more precisely repeatable from one measurement cycle to another. As should be appreciated, a separate one-shot or other circuit could be provided for synchronizing the RF signals in phase at some other predetermined time prior to the detection window of the RF receiver circuitry.

Figure 5:
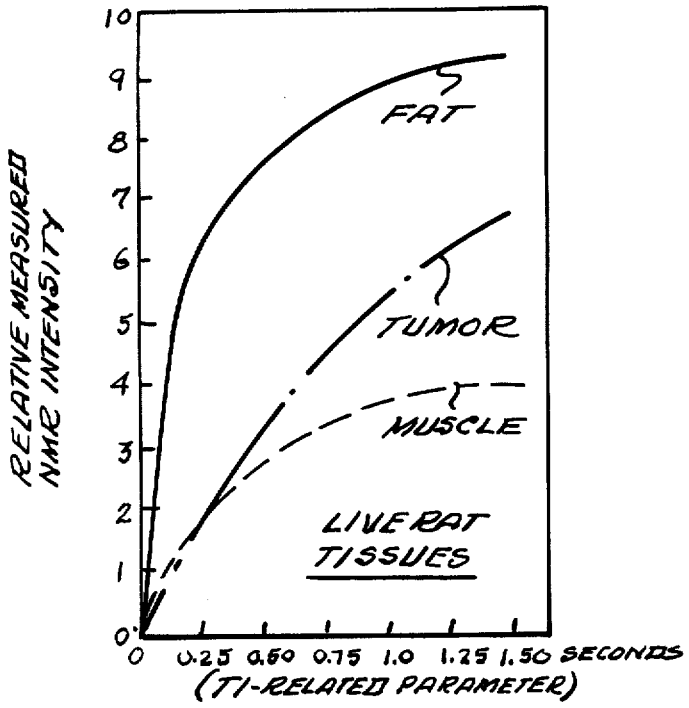
FIG. 5 is a graph showing typical variations in NMR response intensity achieved for various specific tissues of a live rat as a function of the T1-related machine parameter in accordance with an exemplary embodiment of this invention.
Figure 6A:
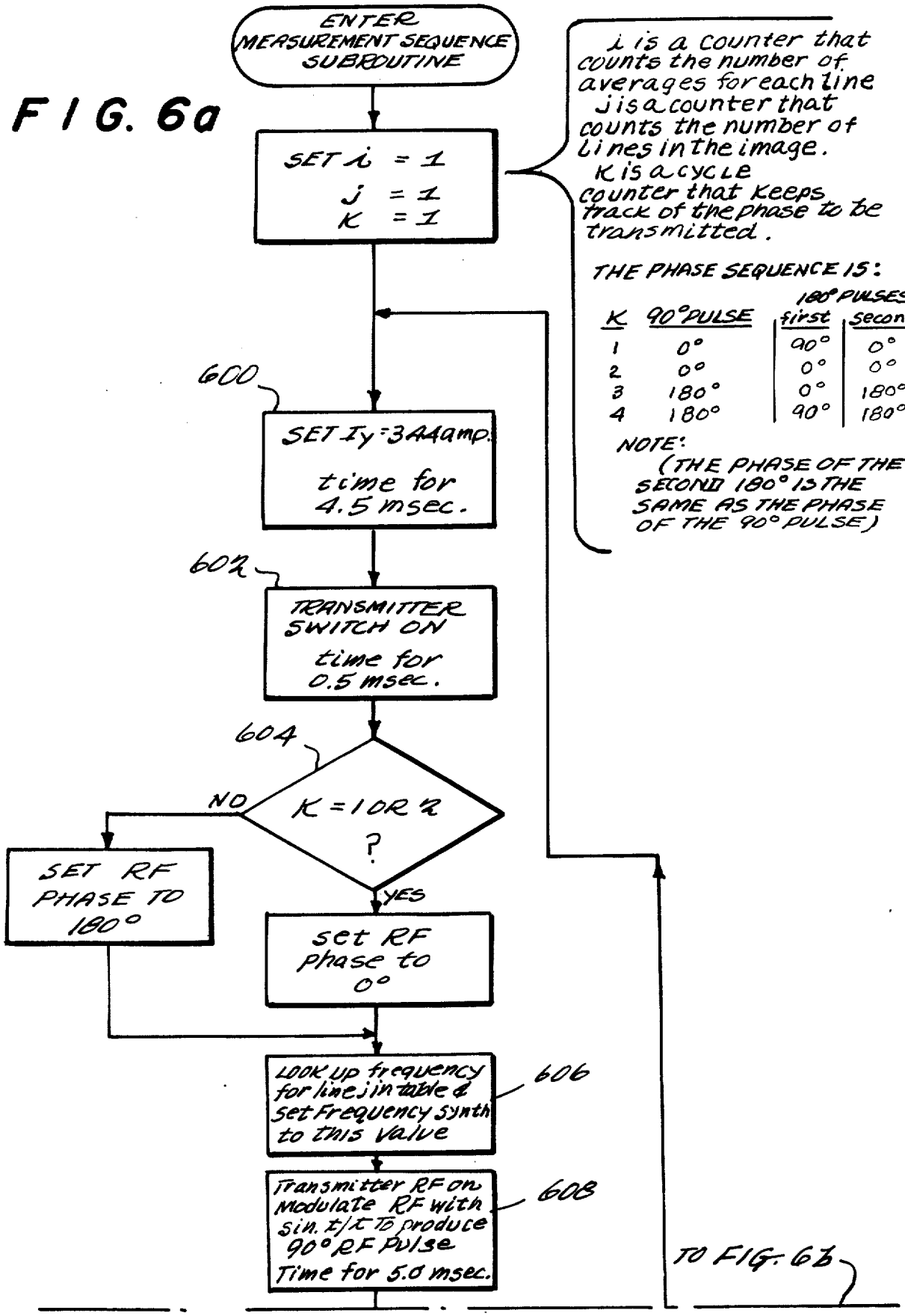
Figure 6B:
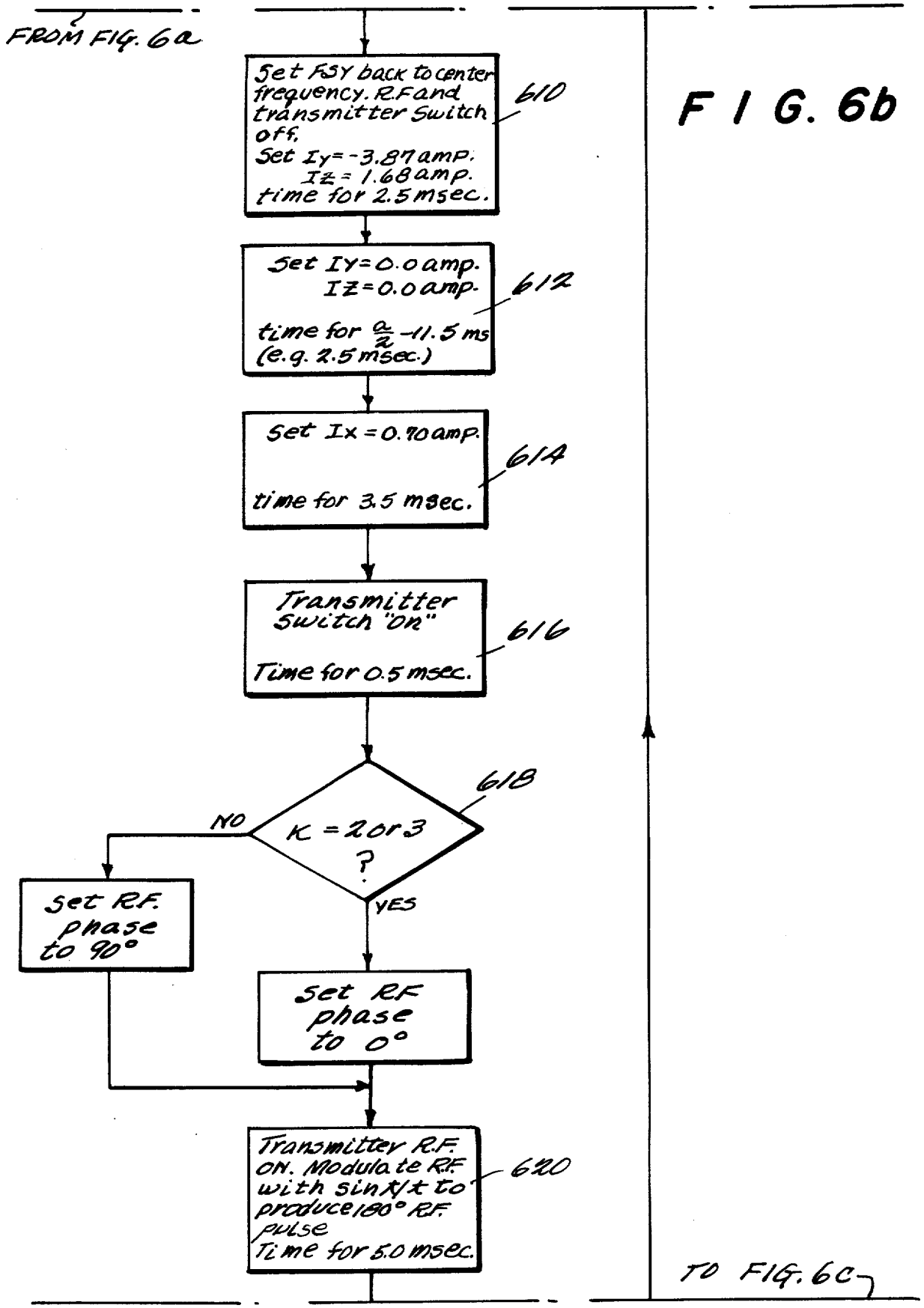
Figure 6C:
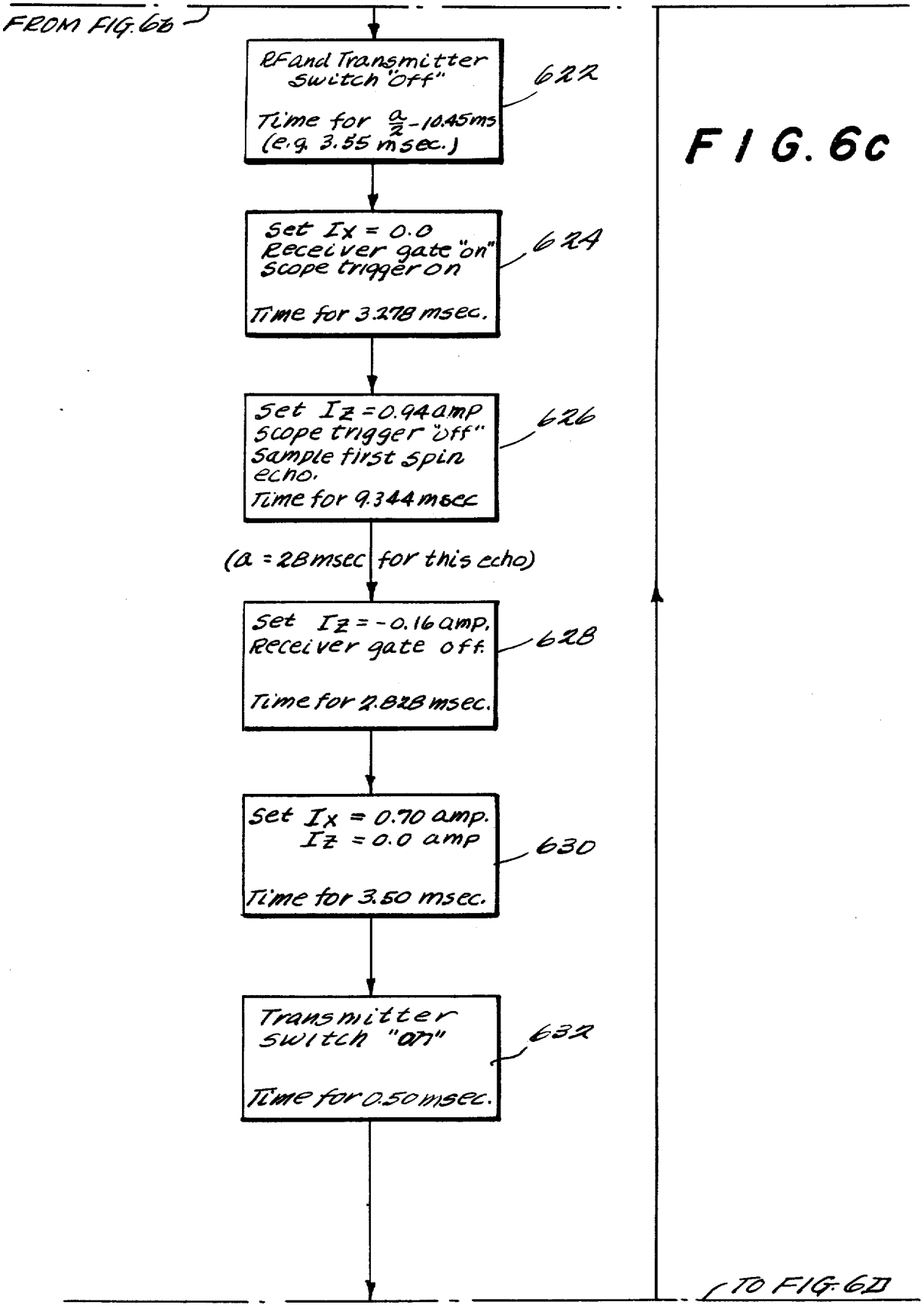
Figure 6D:
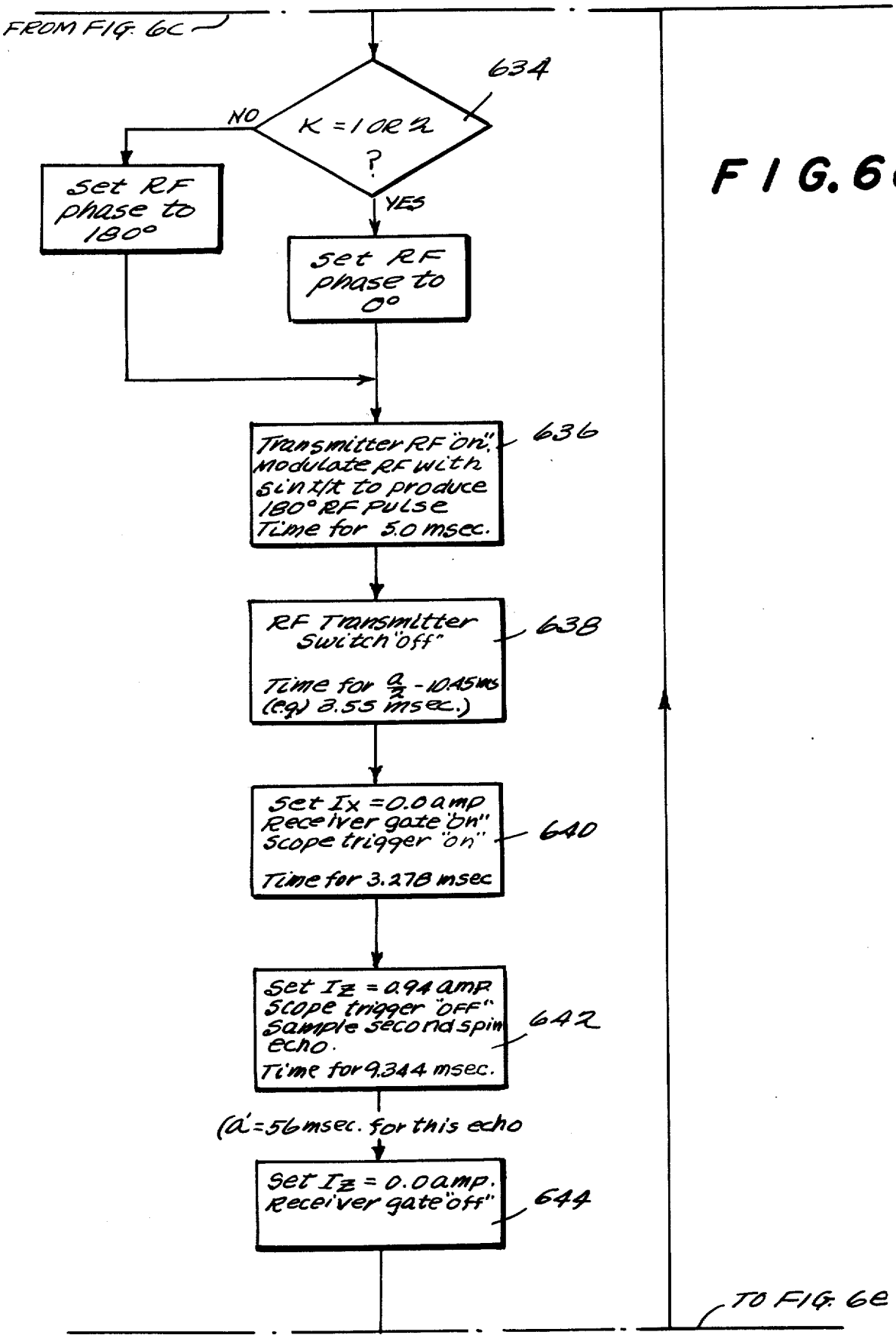
Figure 6E:
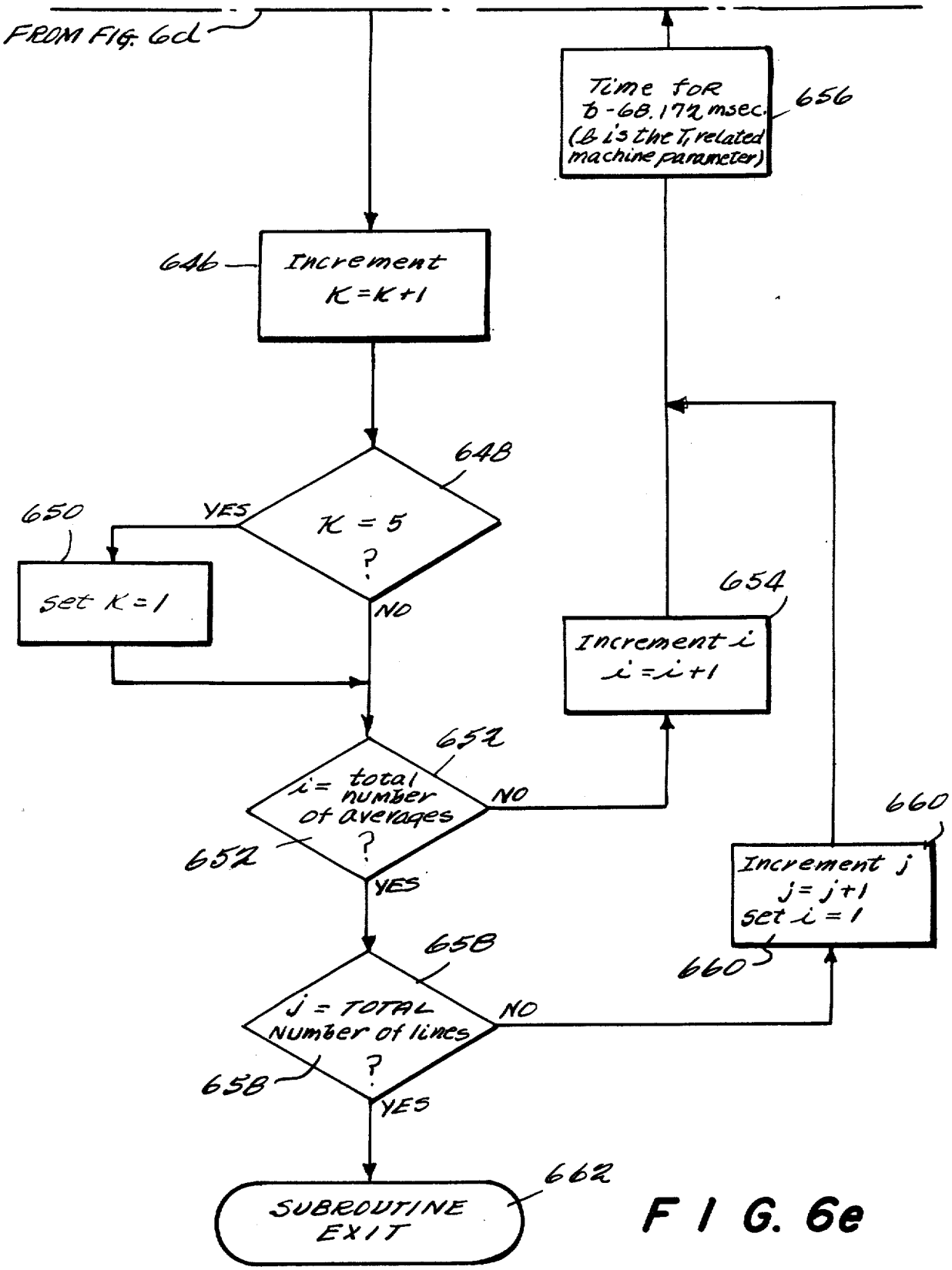

It has been discovered that rather dramatic changes in image contrast can be achieved by selective control of the a and b machine parameters earlier discussed. For example, as shown in FIG. 5, at some values of the b machine parameter, the tumor and muscle tissues of a live rat are virtually indistinguishable with respect to relative measured NMR spin echo intensities detected from measured volumes containing these different tissues. However, as the b parameter is increased, the contrast between these two tissue types becomes greater. At the same time, the contrast between tumor and fat tissues passes through an optimum contrast condition as the b parameter is increased. While it might be expected that better contrast between given tissue types might be expected for an image of T1 parameters than for an image of T2 parameter values, or vice versa, it has been discovered that, in fact, by judicious choice of the a and b machine parameters associated with the exemplary embodiment of this invention, it is often possible to obtain enhanced contrast images which have greater contrast between given tissue types than is available in either an image of T1 values or an image of T2 values. For example, the following Table 2 provides typical values of measured T1 and T2 parameters for specific tissue types (live rat):

TABLE 2

| Typical Measured T1 and T2 Values | | |
|---|---|---|
| Tissue | T1 sec | T2 sec |
| Muscle | 0.65 | 0.031 |
| Liver | 0.45 | 0.040 |
| Fat | 0.30 | 0.054 |
| Brain | 0.79 | 0.053 |
| Hematoma | 0.83 | 0.066 |
| Abscess Pyogenic | 0.57 | 0.058 |
| Abscess Sterile | 0.89 | 0.063 |
| Tumors | 0.94 | 0.058 |

Using these typical T1 and T2 parameter values for particular tissues and assuming equal hydrogen nuclei densities and no motion in all of these tissues, and using the previously described equations, NMR response intensities for different a and b machine parameters can be calculated as shown in the following Table 3:

TABLE 3

| TYPICAL EXPECTED NMR INTENSITIES I | | | | |
|---|---|---|---|---|
| | a = 0.028 sec b = 0.5 sec | a = 0.56 b = 0.5 | a = 0.028 b = 1.0 | a = 0.056 b = 1.0 |
| Muscle | 0.218 | 0.088 | 0.318 | 0.129 |
| Liver | 0.333 | 0.165 | 0.443 | 0.220 |
| Fat | 0.483 | 0.288 | 0.574 | 0.342 |
| Brain | 0.276 | 0.163 | 0.423 | 0.250 |
| Hematoma | 0.296 | 0.194 | 0.458 | 0.300 |
| Abscess Pyogenic | 0.360 | 0.222 | 0.510 | 0.315 |
| Abscess Sterile | 0.276 | 0.177 | 0.433 | 0.278 |
| Tumors | 0.254 | 0.157 | 0.404 | 0.249 |

Using the above calculations, it can be shown that these different selected machine parameter values a and b provide quite different image contrasts between various tissue types where contrast between tissue 1 and tissue 2 is defined as a percentage equal to 100 times the difference in measured intensities between the two tissues divided by the measured intensity of the second tissue. For example, some typical expected image contrast percentages have been calculated in accordance with the data of Tables 2 and 3 as set forth in Table 4 below:

TABLE 4

| Typical Expected Tissue Contrast | | | | |
|---|---|---|---|---|
| | a = 0.028 sec b = 0.5 sec | a = 0.056 b = 0.5 | a = 0.028 b = 1.0 | a = 0.056 b = 1.0 |
| Liver-Muscle | 53% | 88% | 39% | 71% |
| Fat-Muscle | 122% | 227% | 81% | 165% |
| Tumors-Muscle | 17% | 78% | 27% | 93% |
| Tumors-Liver | −24% | −5% | −9% | 13% |
| Hematoma-Brain | 7% | 19% | 8% | 20% |
| Abscess (P)-Muscle | 65% | 152% | 60% | 144% |

Using the same formula for calculating contrast, a straightforward T1 image would have produced a contrast of only about 31% between muscle and liver tissues while a straightforward T2 image would have produced an expected contrast of only about 29%. However, utilizing various a and b machine parameters, an image of measured intensity I (which is a function of a, b, T1 and T2), with a range of contrasts is available from 39% to 88%. Similar examples of enhanced contrast can be seen for other typical entries in these tables. In general, for two tissues 1 and 2 having assumed equal proton densities and T1 NMR parameter values, the optimum machine parameter a can be chosen for maximizing the measured intensity contrast between those images:

$$\Delta I = e^{-a/T2,1} - e^{-b/T2,2} \quad \text{(Equation 3)}$$

$$\frac{d\Delta I}{da} = \frac{1}{T_{2,1}} e^{-a/T2,1} + \frac{1}{T_{2,2}} e^{-a/T2,2} = 0 \quad \text{(Equation 4)}$$

$$a = \frac{T_{2,1}T_{2,2}}{T_{2,1} - T_{2,2}} \ln(T_{2,1}/T_{2,2}) \quad \text{(Equation 5)}$$

Using the above equations, optimum values of the b parameter for fixed assumed equal values of the T2 parameter could also be calculated. It should also be apparent that optimum values for a and b parameters for other given situations can be calculated. In general, the a machine parameter (T2-related) is chosen to have a value between the expected T2 NMR parameter values for the tissues in question. Similiarly, the b machine parameter (T1-related) is chosen to lie between the T1 NMR parameter value for the tissues of interest.

Using these principles, it should be possible by calculation and/or experience to determine optimum machine parameter settings a and b for enhancing the contrast between given types of tissue and thus enhancing the diagnostic capability of the NMR scanner constructed in accordance with the teachings of this invention where the a and b machine parameters can be selectively chosen by the operator.

By performing only two complete measurement sequences of measurement cycles in accordance with this invention, it is possible to calculate both the T1 and T2 NMR parameter values for each elemental measured volume of tissue. Thereafter, using the heretofore defined equations of relationship between the machine a and b parameters and the MNR T1 and T2 parameters, it is possible to mathematically calculate an optimum contrast image of calculated intensity values. On the other hand, if optimum or close to optimum machine a and b parameters are known in advance for enhancing the contrast between given tissue types, then, in accordance with the principles of this invention, a single measurement sequence (of plural measurement cycles as exemplified in FIG. 4) can produce an image of measured NMR intensity values which produces an optimum or near optimum contrast image for distinguishing between selected types of tissues.

Conventional data entry devices are associated with NMR control computer 20 in FIG. 2 to permit selection of a desired machine parameter value for the a and/or b parameters of the exemplary embodiment. For example, as shown, a select machine parameter input 32 is provided. In the preferred exemplary embodiment, the selection means 32 for selecting the a and b machine parameters is the same keyboard used for other operator interfaces with the NMR system control 20. For example, the keyboard is typically incorporated as part of a conventional video display/keyboard input/output terminal device connected to one of the data processors of the NMR system control through the data acquisition and display computer 31 and associated serial line links as shown in FIG. 2. As will be appreciated, separate dedicated switches could also be provided if desired for this machine parameter selection function. In the exemplary embodiment, the a and b parameters are operator selected and are achieved by changing the delay times included in a programmed sequence (shown in detail at FIGS. 6A–6E). Alternatively, the operator could select one of several different programmed sequences, each programmed sequence being designed to effect a particular combination of a and b parameter values.

The particular presently preferred exemplary program sequence for controlling the a and b machine parameters is set forth explicitly at FIGS. 6A–6E. These Figures depict a complete measurement sequence for effecting several measurement cycles as set forth in FIG. 4.

In response to an instruction from the operator, the program sequence for a given complete measurement sequence is entered. As noted in FIG. 6A, control counters I, J and K are initialized to have a contents of 1. Thereafter, at 600, the Y gradient coils are energized with a predetermined current amplitude (e.g. 3.44 amps) for a desired time (e.g. 4.5 milliseconds). Then, at 602, the RF transmitter circuitry is initialized (e.g., connected to the r.f. coil via the r.f. switch) and a small delay (e.g. 0.5 milliseconds) is encountered to ensure that all of the transmitter circuitry is fully ready to operate. Then, at decision point 604, depending upon the value of the K counter contents, either 0 or 180° phase IF signals are selected via the multiplexer 306 in FIG. 3. Thereafter, using a lookup table for the image line volume to be addressed, the frequency synthesizer 300 is set to the appropriate frequency at 606. The transmit RF control signal is then switched "on" so as to trigger the one-shot 320 in FIG. 3 and to enable gate 314. The sinc (t) function is also generated at this time and used to modulate the first 90° nutation pulse X1 which is transmitted for a 5 millisecond duration as shown in box 608.

After the 90° nutation pulse X1 has existed for the requisite time to cause a 90° nutation, the functions at 610 are performed so as to switch the RF on/off control signals to the "off" condition and to set the frequency synthesizer 300 back to its center frequency. At the same time, a Y gradient phase correction current amplitude (e.g. −3.87 amps) and Z gradient phase correction current amplitude (1.68 amps) are set and this condition is maintained for a desired time (e.g. 2.5 milliseconds).

At the conclusion of the gradient phase correction pulses, the Y and Z gradient coil currents are reset to zero at 612 and an additional time delay (e.g. 2.5 milliseconds) is entered. Thereafter, the X gradient coil driver is set to deliver a desired X gradient magnetic field (0.70 amps) and timed for a desired duration (e.g. 3.5 milliseconds) so as to permit the X gradient to reach its desired equilibrium level. At 616, the transmitter circuitry is again initialized and, at 618, depending upon the content of counter K, the multiplex selector 306 is set to select either 0° or 90° phase signals. Then, at 620, the transmitter RF is switched "on" and another sinc(t) modulated pulse is timed (e.g. 5.0 milliseconds) so as to cause a 180° nutation of the selected nuclei in the measured line volume. Thereafter, the 180° nutation Y1 RF pulse is switched off which also results in resetting the phase of reference RF signals supplied to the receiver circuitry.

After some predetermined time (e.g. 355 milliseconds) the X gradient coil is de-energized at 624 and the receiver circuits 26 are gated on in readiness for the receipt of the first spin echo NMR response. In accordance with the earlier time delay occurring between the 90° nutation pulse X1 and the 180° nutation pulse Y1 and the rule of equal times, an additional time delay (3.278 milliseconds) is encountered before the Z gradient coil is set (e.g. at 0.94 amps) at 626 and the first spin echo NMR response signal is sampled (e.g. at 73 microsecond intervals) for the duration of a window (e.g. 9.344 milliseconds corresponding to 128 samples) during which the spin echo signal is expected.

As noted in the Figures, this first spin echo has an a machine parameter of approximately 28 milliseconds for the exemplary sequence shown in the flow chart. This value could of course be adjusted either up or down by selecting different time delays between generation of the 90° nutation pulse and the 180° nutation pulse. For example, the time delays encountered at 612 and possibly at 614 might be adjusted to achieve different a machine parameter values for the first spin echo signal.

At the conclusion of data taking for the first spin echo NMR response, the Z gradient coil is set to provide desired phase correction (e.g. −0.16 amp) and the receiver circuitry is gated off. This condition persists at box 628 for some desired time (e.g. 2.828 milliseconds) before the X gradient coil is set up at 630 for another RF excitation pulse. That is, the Z gradient phase correction is turned off while the X gradient coil is set at some desired value (e.g. 0.70 amps) and permitted to settle out to its equilibrium value (e.g. after a delay of 3.5 milliseconds). Then, at 632, the transmitter circuitry is initialized and after a short delay to ensure readiness (e.g. 0.50 milliseconds), the K counter contents are tested at 634 to determine the setting of multiplexer 306 in FIG. 3. Either a 0° or 180° phase RF signal is thus selected before the transmitter RF is again switched on at 636 and modulated with an appropriate sinc (t) function to produce another 180° nutation RF pulse which persists for some desired time (e.g. 5.0 milliseconds) required to effect a 180° nutation of the nuclei within the selected measurement volume. Thereafter, at 638, the RF pulse is terminated.

As should be appreciated from the earlier discussion, switching the RF on and switching the RF off at 636 and 638 will have each resulted in resetting the relative phase of the RF reference signals produced by the transmitter circuitry in FIG. 3.

After an appropriate time delay (e.g. 3.55 milliseconds), the X gradient coil is switched off at 640 and the receiver circuitry is initialized in anticipation of the second spin echo NMR response. After an appropriate delay to ensure readiness (e.g. 3.278 milliseconds), the Z gradient coil is set up at 642 (e.g. 0.94 amps) and the second spin echo signal is sampled (e.g. at 73 microsecond intervals) for the duration of the second window during which the second spin echo signal is expected (e.g. 9.344 milliseconds). As noted in the Figures, the a parameter for this second spin echo signal is approximately 56 milliseconds. As before, the a parameter associated with the second spin echo response can be either increased or decreased by adjusting appropriate earlier time delays in the measurement cycle as defined in the flow chart.

Thereafter, at 644, the Z gradient coil is turned off as is the receiver at 646 and the K counter is incremented and tested at 648 to see if a quartet of measurement cycles has yet been completed. If a quartet has been completed, the K counter is reset to 1 at 650. Thereafter, at 652, counter I is tested to see if the total number of measurement cycles has been completed for a complete measurement sequence. Typically, 12–14 measurement cycles comprise a complete measurement sequence. If this number of measurement cycles has not yet been achieved, the I counter is incremented at 654 and a time delay is entered at 656 designed to achieve the desired b machine parameter (i.e. the T1-related parameter). After the desired time delay (e.g. b-68.172 milliseconds), control is passed back to 600 for the initiation of another complete measurement cycle.

When the requisite number of measurement cycles have been completed (as tested at decision block 652), the contents of the J counter are tested at 658 to see if all of the line volumes in a given planar volume of interest have been addressed and examined. If not, the J counter is incremented and the I counter is reset to 1 at 600. Control is then passed to the time delay at 656 to achieve the desired b machine parameter before another entire measurement sequence is entered by passing control back to box 600. Eventually, the desired averaged spin echo data will have been collected for all of the line volumes in a given planar volume and the programmed sequence will exit at 662 to some other desired functional control in the NMR system control 20. Typically, this would be the Fourier transformation of all of the accumulated spin echo data so as to generate display pixel values which can thereafter be displayed on a CRT screen as corresponding gray or colored values to visually depict the measured cross-section. As should be apparent from the above discussion, the apparent contrast in such a cross-sectional image between different tissue types will depend not only upon the inherent T1 and/or T2 NMR parameters of the tissue itself but also upon the selection of machine parameters a and b. By making the machine parameters a and b selectable under operator control, enhanced contrast in the resulting image obtained from even a single complete measurement sequence may be obtained. That is, the resultant image of measured NMR response intensities may have a contrast greater than that which would be obtained from a display of either T1 or T2 values per se.

As should also be apparent, a single measurement sequence provides spin echo data for each measured volume having two different "a" machine parameters (T2-related) associated therewith. Accordingly, a best fit to an exponential curve can be achieved using these two data points for each measured volume thus determining the T2 NMR parameter actually associated with that measured volume. By executing another complete measurement sequence utilizing a different "b" machine parameter (T1-related), similar fitting of the measured data to an exponential curve can result in a measured T1 value for each measured volume. Thus, by executing only two complete measurement sequences in accordance with this invention both the T1 and T2 NMR parameters of all elemental measured tissue volumes can be determined and using the equations explained heretofore, an optimum contrast image can be calculated by the data acquisition and display computer 31 and displayed. Alternatively, optimum machine parameters a and b may be predetermined for enhanced or optimum image contrast between selected tissue types and if these machine control parameters a and b are operator selected, a single measurement sequence can result in an enhanced or optimum contrast image of measured I values without the necessity of even performing two measurement sequences (and the measurement cycles could possibly be shortened to one spin echo in this event).

Preferably the time delays embedded within the measurement sequence of FIGS. 6A–6E are operator selected via a keyboard from a continuously or discretely variable spectrum of possibilities. For example, in the exemplary embodiment the a parameter may be varied over a desired range by permitting the operator to key in changes in the various time delay constants employed in the FIG. 6A–6E sequence, using an executive program routine of the type shown in FIG. 7. Alternatively, several different fixed measurement sequences of the type shown in FIG. 6A–6E may be prepared for different timing parameters and selectively entered under operator control as shown in FIG. 8.

While only one specific exemplary embodiment of this invention has been described in detail, those skilled in the art will appreciate that many modifications and variations of this embodiment may be made without departing from the novel and advantageous features of this invention. Accordingly, all such variations and modifications are intended to be included within the scope of the appended claims.

What is claimed is:

[1. An imaging NMR scanner for deriving at least one spin echo NMR r.f. signal from selected internal regions of an object under test in response to applied pulses of transmitted r.f. signals during each of successive measurement cycles, wherein said spin echo NMR r.f. signals have respective amplitudes dependent upon the T1 and T2 NMR parameters of the internal region under test and upon first and second time parameters representing the elapsed times from the beginning of a measurement (a) cycle until the spin echo occurrence and (b) until the beginning of the next measurement cycle, respectively, said scanner comprising:

NMR excitation means capable of selectively controlling said first and second time parameters, and NMR detection means for detecting said spin echo NMR r.f. signals.]

2. An imaging NMR scanner for deriving data representing the internal structures of an object having corresponding T1 and T2 NMR parameters, said scanner comprising:

NMR excitation means for exciting said internal structure to provide plural NMR spin echo output signals during each of successive measurement cycles, said spin echo NMR output signals each having an amplitude dependent upon (1) a first time parameter corresponding to the elapsed time from the beginning of a measurement cycle to the occurrence of the NMR spin echo output signal and (2) a second time parameter corresponding to the elapsed time between the initiation of successive measurement cycles; and control means connected to said excitation means for selectively controlling said first and second time parameters to selectively enhance the detection of differences between the NMR spin echo output signals emanating from different selected ones of said internal structures.

3. An imaging NMR scanner as in claim 2 wherein said NMR excitation means generates pulses of transmitted r.f. signals and includes:

phase control means for accurately controlling the relative phase of said transmitted r.f. signals at the initiation of a pulse thereof.

4. An imaging NMR scanner as in claim 3 wherein said NMR excitation means also generates reference r.f. signals for use in detecting said NMR output signals and wherein:

said phase control means also includes means accurately controlling the relative phase of said reference r.f. signals at a predetermined time prior to the expected time occurrence of said NMR spin echo output signals.

5. An imaging NMR scanner as in claim 4 wherein said phase control means resets the relative phase of said reference r.f. signals at the termination of a pulse of said transmitted r.f. signals.

6. An imaging NMR scanner as in claim 4 wherein said phase control means resets the relative phase of said transmitted r.f. signals at the initiation of each pulse thereof and resets the relative phase of said reference r.f. signals at the termination of each such pulse.

7. A cross-sectional imaging NMR scanner for deriving data representing the internal structure of an object located therewithin, said scanner comprising:

magnetic field generating means for generating controlled magnetic fields having selectable magnitude within a selected measurement volume;

r.f. transmitting means for selectively generating pulses of r.f. electromagnetic fields within said measurement volume having selectable frequency and phase, r.f. receiving means for selectively receiving r.f. electromagnetic fields of predetermined frequency and phase emanating from within said measurement volume;

control means connected to said magnetic field generating means, to said r.f. transmitting means and to said r.f. receiving means for controlling same in predetermined controlled sequences which produce at least two spin echo r.f. signals also containing FID r.f. signal components from said object during each of successive measurement cycles with the relative signs of spin echo and FID signal components being different during at least some of such measurement cycles as compared to others of such measurement cycles; and means for coherently combining respectively corresponding ones of said spin echo r.f. signals resulting from successive measurement cycles to cumulatively enhance the spin echo signal components while simultaneously reducing the FID signal components.

8. A cross-sectional imaging MNR scanner for deriving data representing the internal structure of an object located therewithin, said scanner comprising:

magnetic field generating means for generating controlled magnetic fields having selectable magnitude within a selected measurement volume;

r.f. transmitting means for selectively generating pulses of r.f. electromagnetic fields within said measurement volume having selectable frequency and phase, r.f. receiving means for selectively receiving r.f. electromagnetic fields of predetermined frequency and phase emanating from within said measurement volume;

control means connected to said magnetic field generating means, to said r.f. transmitting means and to said r.f. receiving means for controlling same in a predetermined controlled sequence which produces at least two spin echo r.f. signals from said object during each measurement cycle;

wherein said control means is adapted to cause transmission during each measurement cycle of a 90° nutation RF pulse followed by a 180° nutation RF pulse and, after a first spin echo signal occurs, to cause transmission of a further 180° nutation RF pulse which will thereafter cause a second spin echo signal to occur and wherein the relative phases of said RF pulses during any given measurement cycle are chosen from one line of the following table:

| | Phase of 90° RF Pulse | Phase of 1st 180° RF Pulse | Phase of 2nd 180° RF Pulse |
|---|---|---|---|
| a. | 0° | 0° | 0° |
| b. | 0° | 90° | 0° |
| c. | 0° | 180° | 0° |
| d. | 0° | 270° | 0° |
| e. | 180° | 0° | 180° |
| f. | 180° | 90° | 180° |
| g. | 180° | 180° | 180° |
| h. | 180° | 270° | 180° |

9. A cross-sectional imaging NMR scanner as in claim 8 wherein said control means is adapted to produce measurement cycles in multiples of four, with each such group of four measurement cycles corresponding to four selected ones of said lines a–h in said table, said four lines being chosen to produce a final combined spin echo signal which is non-zero but in which combined FID signal components substantially cancel in accordance with the following continuation of said table:

| | Sign of spin echo | Sign of x plane FID | Sign of y plane FID |
|---|---|---|---|
| a. | − | + | + |
| b. | + | + | + Quadrature |
| c. | − | + | − |
| d. | + | + | − Quadrature |
| e. | + | − | + |
| f. | − | − | + Quadrature |
| g. | + | − | − |
| h. | − | − | − Quadrature |

10. A cross-sectional imaging NMR scanner for deriving data representing the internal structure of an object located therewithin, said scanner comprising:

magnetic field generating means for generating controlled magnetic fields having selectable magnitude within a selected measurement volume;

r.f. transmitting means for selectively generating pulse of r.f. electromagnetic fields within said measurement volume having selectable frequency and phase, r.f. receiving means for selectively receiving r.f. electromagnetic fields of predetermined frequency and phase emanating from within said measurement volume;

control means connected to said magnetic field generating means, to said r.f. transmitting means and to said r.f. receiving means for controlling same in a predetermined controlled sequence which produces at least two spin echo r.f. signals from said object during each measurement cycle;

wherein each of said spin echo r.f. signals have a peak amplitude approximately proportional to $$\exp(-a/T2)1-\exp(-b/T1))/[1+\exp(-b/T2)\exp(-b/T1)]$$

where a = a first time parameter corresponding to the elasped time from the beginning of a measurement cycle to the spin echo signal peak, b = a second time parameter corresponding to the elapsed time between successive measurement cycles, T1 = the NMR longitudinal time constant of the measured volume, T2 = the NMR transverse time constant of the measured volume;

and wherein said control means is adapted to selectively vary said first and second time parameters so as to enhance the resultant contrast between differing parts of said internal structure.

11. A cross-sectional imaging NMR scanner for deriving data representing the internal structure of an object located therewithin, said scanner comprising:

magnetic field generating means for generating controlled magnetic fields having selectable magnitude within a selected measurement volume;

r.f. transmitting means for selectively generating pulse of r.f. electromagnetic fields within said measurement volume having selectable frequency and phase, r.f. receiving means for selectively receiving r.f. electromagnetic fields of predetermined frequency and phase emanating from within said measurement volume;

control means connected to said magnetic field generating means, to said r.f. transmitting means and to said r.f. receiving means for controlling same in a predetermined controlled sequence which produces at least two spin echo r.f. signals from said object during each measurement cycle;

wherein said r.f. transmitting means includes phase control reset means for accurately resetting the relative phase of said r.f. fields at the initiation of each of said pulses.

12. A cross-sectional imaging NMR scanner as in claim 11 wherein said transmitting means is connected to provide r.f. reference signals to said r.f. receiving means subsequent to at least selected ones of said pulses, and wherein said pulse control reset means also accurately resets the relative phase of said r.f. reference signals at the termination of or subsequent to said selected ones of said pulses.

13. A cross-sectional imaging NMR scanner as in claim 10 wherein said a and b parameters are selected via said control means to enhance the contrast between a first part of said internal structure having T1′ and T2′ NMR parameters and a second part of said internal structure having T1″ and T2″ NMR parameters by causing said a parameter to have a value between the T2′ and T2″ values and by causing said b parameter to have a value between the T1′ and T1″ values.

14. A cross-sectional imaging NMR scanner as in claim 13 wherein said control means includes means for selecting the a parameter value approximately as defined by the equation:

$$a=[T2'T2''\ln(T2'/T1'')]/(T2'-T2'').$$

[15. An imaging NMR scanner for deriving data representing internal structure of an object having corresponding T1 and T2 NMR parameters, said scanner comprising:

NMR excitation means for exciting said internal structure to provide at least one NMR spin echo output signal during each of successive measurement cycles, said NMR spin echo output signals having an amplitude approximately proportional to $$\exp(-a/T2)[1-\exp(-b/T1)]$$

where a = a first time parameter corresponding to the elapsed time from the beginning of a measurement cycle to the NMR spin echo output signal, b = a second time parameter corresponding to the elapsed time between successive measurement cycles;

NMR detection means for detectin9 said NMR spin echo output signals; and measurement control means connected to said NMR excitation means for controlling at least one of said first and second time parameters so as to enhance the resultant contrast between differing parts of said internal structure.]

[16. An imaging NMR scanner as in claim 15 wherein said control means includes means for selecting said a and b parameters to enhance the contrast between a first part of said internal structure having T1′ and T2′ NMR parameters and a second part of said internal structure having T1″ and T2″ NMR parameters by selecting the a parameter to have a value between the T2′ and T2″ values and by selecting the b parameter to have a value between the T1′ and T1″ values.]

17. An imaging NMR scanner [as in claim 16] *for deriving data representing internal structure of an object having corresponding T1 and T2 NMR parameters, said scanner comprising:*

*NMR excitation means for exciting said internal structure to provide at least one NMR spin echo output signal during each of successive measurement cycles, said NMR spin echo output signals having an amplitude approximately proportional to*

$$\exp(-a/T2)[1-\exp(-b/T1)]$$

*where*

*a = a first time parameter corresponding to the elapsed time from the beginning of a measurement cycle to the NMR spin echo output signal,*

*b = a second time parameter corresponding to the elapsed time between successive measurement cycles;*

*NMR detection means for detecting said NMR spin echo output signals; and*

*measurement control means connected to said NMR excitation means for controlling at least one of said first and second time parameters so as to enhance the resultant contrast between differing parts of said internal structure; wherein said control means includes means for selecting said a and b parameters to enhance the contrast between a first part of said internal*

*structure having T1' and T2' NMR parameters and a second part of said internal structure having T1" and T2" NMR parameters by selecting the a parameter to have a value between the T2' and T2" values and by selecting the b parameter to have a value between the T1' and T1" values* wherein said control means is adapted to cause transmission during each measurement cycle of a 90° nutation RF pulse followed by a 180° nutation RF pulse and, after a first spin echo signal occurs, to cause transmission of a further 180° RF pulse which will thereafter cause a second spin echo signal to occur and wherein the relative phases of said RF pulses during any given measurement cycle are chosen from one line of the following table:

| | Phase of 90° RF Pulse | Phase of 1st 180° RF Pulse | Phase of 2nd 180° RF Pulse |
|---|---|---|---|
| a. | 0° | 0° | 0° |
| b. | 0° | 90° | 0° |
| c. | 0° | 180° | 0° |
| d. | 0° | 270° | 0° |
| e. | 180° | 0° | 180° |
| f. | 180° | 90° | 180° |
| g. | 180° | 180° | 180° |
| h. | 180° | 270° | 180° |

18. An imaging NMR scanner as in claim [15, 16 or] 17 wherein said NMR excitation means produces successive pulses of RF fields through said object and wherein said excitation means includes an r.f. signal generator producing r.f. signals and a phase control reset means for accurately resetting the relative phase of said r.f. signals at the initiation of each of said pulses.

19. An imaging NMR scanner as in claim 18 wherein said r.f. signal generator provides reference r.f. signals to said NMR detection means and said phase control reset means also accurately resets the relative phase of said reference r.f. signals at least once during each measurement cycle.

20. An imaging NMR scanner as in claim 19 wherein said phase control means resets the relative phase of said reference r.f. signals at the termination of each of said pulses.

[21. An imaging NMR scanner for deriving enhanced contrast data representing first and second internal structures of an object, said structures having T1', T2' and T1", T2" NMR parameters, respectively, said scanner comprising:

NMR excitation means for exciting said object to provide NMR spin echo output signals during successive measurement cycles, said NMR output signals having an amplitude approximately proportional to $$\exp(-a(T2)(1-\exp(-b/T1))/[1+\exp(-b/T2)\exp(-b/T1)$$

where a = a first time parameter corresponding to the elapsed time from the beginning of a measurement cycle to said NMR spin echo output signal, b = a second time parameter corresponding to the elapsed time between successive measurement cycles, T1 = the NMR longitudinal time constant of the measured volume T2 = the NMR transverse time constant of the measured volume; and excitation control means for selecting values for said first and second time parameters which enhance the contrast between NMR signals obtained from said first and second internal structures respectively.]

[22. An imaging NMR scanner as in claim 21 wherein said control means includes means for selecting the value of said first time parameter between the T2' and T2" values and for selecting the value of said second time parameter between the T1' and T1" values.]

[23. An imaging NMR scanner as in claim 22 wherein said control means includes means for selecting the a parameter value approximately as defined by the equation:

$$a=[T2'T2''\ln(T2'/T2'')]/(T2'-T2'').]$$

24. An imaging NMR scanner [as in claim 21, 22, or 23] *for deriving enhanced contrast data representing first and second internal structures of an object, said structures having T1', T2' and T1", T2" NMR parameters, respectively, said scanner comprising:*

*NMR excitation means for exciting said object to provide NMR spin echo output signals during successive measurement cycles, said NMR output signals having an amplitude approximately proportional to*

$$\exp(-a/T2)(1-\exp(-b/T1))/[1+\exp(-b/T2)\exp(-b/T1)]$$

*where*

*a = a first time parameter corresponding to the elapsed time from the beginning of a measurement cycle to said NMR spin echo output signal,*

*b = a second time parameter corresponding to the elapsed time between successive measurement cycles,*

*T1 = the NMR longitudinal time constant of the measured volume*

*T2 = the NMR transverse time constant of the measured volume; and*

*excitation control means for selecting values for said first and second time parameters which enhance the contrast between NMR signals obtained from said first and second internal structures respectively;* wherein said NMR excitation means produces successive pulses of RF fields through said object and wherein said excitation means includes an r.f. signal generator producing r.f. signals and a phase control reset means for accurately resetting the relative phase of said r.f. signals at the initiation of each of said pulses.

25. An imaging NMR scanner as in claim 24 wherein said r.f. signal generator provides r.f. reference signals and said phase control reset means also accurately resets the relative phase of said reference r.f. signals at least once during each measurement cycle.

26. An imaging NMR scanner as in claim 25 wherein said phase control means resets the relative phase of said reference r.f. signals at the termination of each of said pulses.

27. An improved imaging NMR scanner of the type including NMR excitation means for generating r.f. NMR responses from an object to be imaged and including r.f. signal generator means generating reference r.f. signals for use in synchronously detecting said r.f. NMR responses and also generating pulses of transmitted r.f. signals to be transmitted into said object for causing the production of said r.f. NMR responses wherein the improvement comprises:

phase control reset means for accurately resetting the relative phase of said transmitted r.f. signals at the initiation of said pulses.

28. An improved NMR scanner of the type including NMR excitation means for generating r.f. NMR responses from an object to be imaged and including r.f. signal generator means generating reference r.f. signals for use in synchronously detecting said r.f. NMR responses and also generating pulses of transmitted r.f. signals to be transmitted into said object for causing the production of said r.f. NMR responses wherein the improvement comprises:

phase control reset means for accurately resetting the relative phase of said transmitted r.f. signals at the initiation of said pulses; and wherein said phase control reset means also accurately resets the relative phase of said reference r.f. signals at the termination of or subsequent of said pulses.

[29. An NMR imaging method for deriving at least one spin echo NMR r.f. signal from selected internal regions of an object under test in response to applied pulses of transmitted r.f. signals during each of successive measurement cycles, wherein said spin echo NMR r.f. signals have respective amplitudes dependent upon the T1 and T2 NMR parameters of the internal region under test and upon first and second time parameters representing the elapsed times from the beginning of a measurement (a) cycle until the spin echo occurrence and (b) until the beginning of the next measurement cycle, respectively, said method comprising:

selectively controlling said first and second time parameters, and detecting said spin echo NMR r.f. signals.]

30. A method for deriving NMR imaging data representing the internal structures of an object having corresponding T1 and T2 NMR parameters, said method comprising:

exciting said internal structure to provide plural NMR spin echo output signals during each of successive measurement cycles, said spin echo NMR output signals each having an amplitude dependent upon (1) a first time parameter corresponding to the elapsed time from the beginning of a measurement cycle to the occurrence of the NMR spin echo output signal and (2) a second time parameter corresponding to the elapsed time between the initiation of successive measurement cycles; and selectively controlling said first and second time parameters to selectively enhance the detection of differences between the NMR spin echo output signals emanating from different selected ones of said internal structures.

31. A method as in claim 30 wherein said exciting step includes the generation of pulses of transmitted r.f. signals and further comprises:

accurately controlling the relative phase of said transmitted r.f. signals at the initiation of a pulse thereof.

32. A method as in claim 31 wherein said exciting step also generates reference r.f. signals for use in detecting said NMR output signals and includes:

accurately controlling the relative phase of said reference r.f. signals at a predetermined time prior to the expected time occurrence of said NMR spin echo output signals.

33. A method as in claim 32 wherein the relative phase of said reference r.f. signals is reset at the termination of a pulse of said transmitted r.f. signals.

34. A method as in claim 32 wherein the relative phase of said transmitted r.f. signals is reset at the initiation of each pulse thereof and the relative phase of said reference r.f. signals is reset at the termination of each such pulse.

35. A method of NMR imaging deriving data representing the internal structure of an object located therewithin, said method comprising:

generating controlled magnetic fields having selectable magnitude within a selected measurement volume;

selectively generating pulses of r.f. electromagnetic fields within said measurement volume having selectable frequency and phase;

selectively receiving r.f. electromagnetic fields of predetermined frequency and phase emanating from within said measurement volume;

controlling the aforesaid steps in predetermined controlled sequences which produce at least two spin echo r.f. signals also containing FID signal components from said object during each of successive measurement cycles with the relative signs of spin echo and FID signal components being different during at least some of such measurement cycles as compared to others of such measurement cycles; and coherently combining respectively corresponding ones of said spin echo r.f. signals resulting from successive measurement cycles to cumulatively enhance the spin echo signal components while simultaneously reducing the FID signal components.

36. A method of NMR imaging derived data representing the internal structure of an object located therewithin, said method comprising:

generating controlled magnetic fields having selectable magnitude within a selected measurement volume;

selectively generating pulses of r.f. electromagnetic fields within said measurement volume having selectable frequency and phase;

selectively receiving r.f. electromagnetic fields of predetermined frequency and phase emanating from within said measurement volume;

controlling the aforesaid steps in a predetermined controlled sequence which produces at least two spin echo r.f. signals from said object during each measurement cycle;

wherein said controlling step causes transmission during each measurement cycle of a 90° nutation RF pulse followed by a 180° nutation RF pulse and, after a first spin echo signal occurs, causes transmission of a further 180° nutation RF pulse which will thereafter cause a second spin echo signal to occur and wherein the relative phases of said RF pulses during any given measurement cycle are chosen from one line of the following table:

| | Phase of 90° RF Pulse | Phase of 1st 180° RF Pulse | Phase of 2nd 180° RF Pulse |
|---|---|---|---|
| a. | 0° | 0° | 0° |
| b. | 0° | 90° | 0° |
| c. | 0° | 180° | 0° |

-continued

| | Phase of 90° RF Pulse | Phase of 1st 180° RF Pulse | Phase of 2nd 180° RF Pulse |
|---|---|---|---|
| d. | 0° | 270° | 0° |
| e. | 180° | 0° | 180° |
| f. | 180° | 90° | 180° |
| g. | 180° | 180° | 180° |
| h. | 180° | 270° | 180° |

37. A method as in claim 36 wherein said controlling step produces measurement cycles in multiples of four, with each such group of four measurement cycles corresponding to four selected ones of said lines a–h in said table, said four lines being chosen to produce a final combined spin echo signal which is non-zero but in which combined FID signal components substantially cancel in accordance with the following continuation of said table:

| | Phase of 90° RF Pulse | Phase of 1st 180° RF Pulse | Phase of 2nd 180° RF Pulse |
|---|---|---|---|
| a. | 0° | 0° | 0° |
| b. | 0° | 90° | 0° |
| c. | 0° | 180° | 0° |
| d. | 0° | 270° | 0° |
| e. | 180° | 0° | 180° |
| f. | 180° | 90° | 180° |
| g. | 180° | 180° | 180° |
| h. | 180° | 270° | 180° |

38. A method of NMR imaging deriving data representing the internal structure of an object located therewithin, said method comprising:

generating controlled magnetic fields having selectable magnitude within a selected measurement volume;

selectively generating pulses of r.f. electromagnetic fields within said measurement volume having selectable frequency and phase;

selectively receiving r.f. electromagnetic fields of predetermined frequency and phase emanating from within said measurement volume;

controlling the aforesaid steps in a predetermined controlled sequence which produces at least two spin echo r.f. signals from said object during each measurement cycle;

wherein each of said spin echo r.f. signals have a peak amplitude approximately proportional to $$\exp(-a/T2)(1-\exp(-b/T1))/[1+\exp(-b/T2)\exp(-b/T1)]$$

where a = a first time parameter corresponding to the elapsed time from the beginning of a measurement cycle to the spin echo signal peak, b = a second time parameter corresponding to the elapsed time between successive measurement cycles, T1 = the NMR longitudinal time constant of the measured volume;

T2 = the NMR transverse time constant of the measured volume;

and wherein said controlling step selectively varies said first and second time parameters so as to enchance the resultant contrast between differing parts of said internal structure.

39. A method of NMR imaging deriving data representing the internal structure of an object located therewithin, said method comprising:

generating controlled magnetic fields having selectable magnitude within a selected measurement volume;

selectively generating pulses of r.f. electromagnetic fields within said measurement volume having selectable frequency and phase;

selectively receiving r.f. electromagnetic fields of predetermined frequency and phase emanating from within said measurement volume;

controlling the aforesaid steps in a predetermined controlled sequence which produces at least two spin echo r.f. signals from said object during each measurement cycle;

wherein said generating pulses of r.f. step comprises accurately resetting the relative phase of said r.f. fields at the initiation of each of said pulses.

40. A method as in claim 39 including the step of generating r.f. reference signals for use in said r.f. receiving step subsequent to at least selected ones of said pulses, and including the step of accurately resetting the relative phase of said r.f. reference signals at the termination of or subsequent to said selected ones of said pulses.

41. A method as in claim 38 wherein said a and b parameters are selected to enhance the contrast between a first part of said internal structure having T1′ and T2′ NMR parameters and a second part of said internal structure having T1″ and T2″ NMR parameters by choosing said a parameter to have a value between the T2′ and T2″ values and by choosing said b parameter to have a value between the T1′ and T1″ values.

42. A method as in claim 41 wherein said controlling step includes selecting the a parameter value approximately as defined by the equation:

$$a=[T2'T2''\ln(T2'/T1'')]/(T2'-T2'').$$

[43. A method for deriving NMR data representing internal structure of an object having corresponding T1 and T2 NMR parameters, said method comprising:

exciting said internal structure to provide at least one NMR spin echo output signal during each of successive measurement cycles, said NMR spin echo output signals having an amplitude approximately proportional to $$\exp(-a/T2)[1-\exp(-b/T1)]$$

where a = a first time parameter corresponding to the elapsed time from the beginning of a measurement cycle to the NMR spin echo output signal, b = a second time parameter corresponding to the elapsed time between successive measurement cycles;

detecting said NMR spin echo output signals; and controlling at least one of said first and second time parameters so as to enhance the resultant contrast between differeing parts of said internal structure.]

[44. A method as in claim 43 wherein said controlling step includes selecting said a and b parameters to enhance the contrast between a first part of said internal structure having T1′ and T2′ NMR parameters and a second part of said internal structure having T1" and T2" NMR parameters by selecting the a parameter to have a value between the T2' and T2" values and by selecting the b parameter to have a value between the T1' and T1" values.]

45. A method [as in claim 44] *for deriving NMR data representing internal structure of an object having corresponding T1 and T2 NMR parameters, and said method comprising:*

*exciting said internal structure to provide at least one NMR spin echo output signal during each of successive measurement cycles, said NMR spin echo output signals having an amplitude approximately proportional to*

$$exp(-a/T2)[1-exp(-b/T1)]$$

*where*

*a = a first time parameter corresponding to the elapsed time from the beginning of a measurement cycle to the NMR spin echo output signal,* b = a second time parameter corresponding to the elapsed time between successive measurement cycles;

*detecting said NMR spin echo output signals; and*

*controlling at least one of said first and second time parameters so as to enhance the resultant contrast between differing parts of said internal structure; wherein said controlling step includes selecting said a and b parameters to enhance the contrast between a first part of said internal structure having T1' and T2' NMR parameters and a second part of said internal structure having T1" and T2" NMR parameters by selecting the a parameter to have a value between the T2' and T2" values and by selecting the b parameter to have a value between the T1' and T1" values;* wherein said controlling step causes transmission during each measurement cycle of a 90° nutation RF pulse followed by a 180° nutation RF pulse and, after a first spin echo signal occurs, causes transmission of a further 180° RF pulse which will thereafter cause a second spin echo signal to occur and wherein the relative phases of said RF pulses during any given measurement cycle are chosen from one line of the following table:

| | Phase of 90° RF Pulse | Phase of 1st 180° RF Pulse | Phase of 2nd 180° RF Pulse |
|---|---|---|---|
| a. | 0° | 0° | 0° |
| b. | 0° | 90° | 0° |
| c. | 0° | 180° | 0° |
| d. | 0° | 270° | 0° |
| e. | 180° | 0° | 180° |
| f. | 180° | 90° | 180° |
| g. | 180° | 180° | 180° |
| h. | 180° | 270° | 180° |

46. A method as in claim [43, 44 or 15] *45* wherein said excitation step produces successive pulses of RF fields through said object and wherein said excitation step includes producing r.f. signals and for accurately resetting the relative phase of said r.f. signals at the initiation of each of said pulses.

47. A method as in claim 46 wherein reference r.f. signals are generated for said NMR detection step including accurately resetting the relative phase of said reference r.f. signals at least once during each measurement cycle.

48. A method as in claim 47 wherein the relative phase of said reference r.f. signals is reset at the termination of each of said pulses.

[49. A method for deriving enhanced contrast NMR data representing first and second internal structures of an object, said structures having T1', T2' and T1", T2" NMR parameters, respectively, said method comprising:

exciting said object to provide NMR spin echo output signals during successive measurement cycles, said NMR output signals having an amplitude approximately proportional to $$exp(-a/T2)(1-exp(-b/T1))/[1+exp(-b/T2)exp(-b/T1)]$$

where a = a first time parameter corresponding to the elapsed time from the beginning of a measurement cycle to said NMR spin echo output signal, b = a second time parameter corresponding to the elapsed time between successive measurement cycles, T1 = the NMR longitudinal time constant of the measured volume T2 = the NMR transverse time constant of the measured volume; and selecting values for said first and second time parameters which enhance the contrast between NMR signals obtained from said first and second internal structures respectively.]

[50. A method as in claim 49 wherein said selecting step includes selecting the value of said first time parameter between the T2' and T2" values and for selecting the value of said second time parameter between the T1' and T1" values.]

[51. A method as in claim 50 wherein said selecting step includes selecting the a parameter value approximately as defined by the equation:

$$a=[T2'T2''\ln(T2'/T2'')]/(T2'-T2'').]$$

52. A method [as in claim 49, 50 or 51] *for deriving enhanced contrast NMR data representing first and second internal structures of an object, said structures having T1', T2' and T1", T2" NMR parameters, respectively, said method comprising:*

*exciting said object to provide NMR spin echo output signals during successive measurement cycles, sand NMR output signals having an amplitude approximately proportional to*

$$exp(-1/T2)(1-exp(-b/T1))/[1-exp(-b/T2)exp(-b/T1)]$$

*where*

*a = a first time parameter corresponding to the elapsed time from the beginning of a measurement cycle to said NMR spin echo output signal,*

*b = a second time parameter corresponding to the elapsed time between successive measurement cycles,*

*T1 = the NMR longitudinal time constant of the measured volume*

*T2 = the NMR transverse time constant of the measured volume; and*

*selecting values for said first and second time parameters which enhance the contrast between NMR signals obtained from said first and second internal structures respectively;* wherein said NMR excitation step produces successive pulses of RF fields through said object and wherein said excitation step includes producing r.f. signals and accurately resetting the relative phase of said r.f. signals at the initiation of each of said pulses.

53. A method as in claim 52 wherein said r.f. signal producing step also provides r.f. reference signals and also accurately resets the relative phase of said reference r.f. signals at least once during each measurement cycle.

54. A method as in claim 53 wherein the relative phase of said reference r.f. signals is reset at the termination of each of said pulses.

55. An improved imaging NMR method of the type including generating r.f. NMR responses from an object to be imaged, generating reference r.f. signals for use in synchronously detecting said r.f. NMR responses and also generating pulses of transmitted r.f. signals to be transmitted into said object for causing the production of said r.f. NMR responses wherein the improvement comprises:

accurately resetting the relative phase of said transmitted r.f. signals at the initiation of said pulses.

56. An improved imaging NMR method of the type including generating r.f. NMR responses from an object to be imaged, generating reference r.f. signals for use in synchronously detecting said r.f. NMR responses and also generating pulses of transmitted r.f. signals to be transmitted into said object for causing the production of said r.f. NMR responses wherein the improvement comprises:

accurately resetting the relative phase of said transmitted r.f. signals at the initiation of said pulses; and resetting the relative phase of said reference r.f. signals at the termination of or subsequent to said pulses.

57. A method of rapidly generating NMR signal responses from plural respectively corresponding portions of an object for use in NMR imaging thereof, said method comprising the steps of:

(a) selectively exciting a first predetermined volume of the object with a 90° r.f. nutation pulse;

(b) subsequently selectively exciting a second predetermined volume of the object with a 180° r.f. nutation pulse;

(c) said first and second predetermined volumes substantially intersecting and overlapping so as to elicit an NMR spin echo from their common overlapping volume; and (d) repeating steps (a)–(c) for further intersecting overlapping volumes outside of previously excited volumes within the spin-lattice relaxation time T1 of the first predetermined volume.

58. An NMR imaging method wherein NMR signals are rapidly generated for imaging plural planar volumes, said method comprising the steps of:

(a) selectively exciting a predetermined volume to generate an NMR response by successively exciting two regions which overlap to thereby define said predetermined volume; and (b) repeating step (a) for further predetermined volumes outside of previously excited regions within the spin-lattice relaxation time T1 of the first selected predetermined volume.

* * * * *